United States Patent
Trimble

(10) Patent No.: US 11,890,118 B2
(45) Date of Patent: Feb. 6, 2024

(54) PATIENT SUPPORT APPARATUS WITH SUPPORT ASSEMBLY FOR MEDICAL DEVICE

(71) Applicant: Stryker Corporation, Kalamazoo, MI (US)

(72) Inventor: Shawn Trimble, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/702,891

(22) Filed: Mar. 24, 2022

(65) Prior Publication Data

US 2022/0304760 A1 Sep. 29, 2022

Related U.S. Application Data

(60) Provisional application No. 63/165,382, filed on Mar. 24, 2021.

(51) Int. Cl.
*A61B 50/13* (2016.01)
*A61G 1/04* (2006.01)

(52) U.S. Cl.
CPC ............... *A61B 50/13* (2016.02); *A61G 1/04* (2013.01)

(58) Field of Classification Search
CPC ...... A61G 2203/78; A61G 1/04; A61G 13/10; A61G 13/101; A61B 50/13
See application file for complete search history.

(56) References Cited

U.S. PATENT DOCUMENTS

| 2,678,792 A * | 5/1954 | Gallion | A47B 23/02 |
| | | | 5/503.1 |
| 2,703,265 A * | 3/1955 | Wolfe | A47B 23/02 |
| | | | 5/503.1 |

(Continued)

FOREIGN PATENT DOCUMENTS

| CN | 106074017 A | 11/2016 |
| WO | 2021062558 A1 | 4/2021 |

(Continued)

OTHER PUBLICATIONS

English language abstract and machine-assisted English translation for CN 106074017 A extracted from espacenet.com database on May 23, 2022, 9 pages.

*Primary Examiner* — Justin C Mikowski
*Assistant Examiner* — Adam C Ortiz
(74) *Attorney, Agent, or Firm* — Howard & Howard Attorneys PLLC

(57) ABSTRACT

A patient support apparatus for concurrently transporting a patient and a medical device includes a base and an intermediate frame coupled to the base and further includes a support assembly coupled to the intermediate frame. The support assembly supports the medical device for concurrent movement with the patient support apparatus. The support assembly includes a track extending between first and second track ends with at least one curvilinear region defined therebetween and includes a carrier for selective movement between the ends. The support assembly also includes a mount coupled to the track and configured to support the medical advice. The support assembly further includes a retainer operatively attached to the carrier with the carrier operable between an engaged state to inhibit relative movement of the carrier along the track and a disengaged state to permit movement of the carrier along the track.

21 Claims, 20 Drawing Sheets

(56) References Cited

U.S. PATENT DOCUMENTS

| | | | |
|---|---|---|---|
| 2,749,196 A * | 6/1956 | Wolfe | A47B 23/025 248/228.3 |
| 3,054,122 A * | 9/1962 | Sarkus | A47B 23/02 108/49 |
| 4,557,453 A | 12/1985 | McCloskey | |
| 4,602,756 A * | 7/1986 | Chatfield | F16M 11/045 403/80 |
| 5,362,021 A | 11/1994 | Phillips | |
| 5,806,111 A | 9/1998 | Heimbrock et al. | |
| 5,839,136 A | 11/1998 | Vance et al. | |
| 5,845,351 A | 12/1998 | Berta et al. | |
| 6,471,167 B1 | 10/2002 | Myers et al. | |
| 6,493,890 B2 | 12/2002 | Smeed | |
| 7,082,882 B2 | 8/2006 | Heimbrock | |
| 7,376,992 B2 | 5/2008 | Salt et al. | |
| 7,398,571 B2 | 7/2008 | Souke et al. | |
| 7,719,437 B2 | 5/2010 | Bertram, III | |
| 8,302,231 B2 | 11/2012 | Moffitt et al. | |
| 8,650,682 B2 | 2/2014 | Herman | |
| 8,752,220 B2 | 6/2014 | Soderberg et al. | |
| 8,915,478 B2 | 12/2014 | Perez | |
| 9,730,851 B2 | 8/2017 | Clark et al. | |
| 9,750,657 B2 | 9/2017 | Drake | |
| 10,028,875 B2 | 7/2018 | Hatch | |
| 10,307,313 B2 | 6/2019 | Schroeder et al. | |
| 10,561,547 B2 | 2/2020 | Doak | |
| 10,582,981 B2 | 3/2020 | Childs et al. | |
| 10,729,602 B2 | 8/2020 | Smeed | |
| 10,799,404 B2 | 10/2020 | Harris | |
| 10,987,268 B2 | 4/2021 | Souke et al. | |
| 11,103,398 B2 | 8/2021 | Zerhusen et al. | |
| 11,213,439 B2 * | 1/2022 | Chinn | A61G 1/0231 |
| 2006/0031989 A1 * | 2/2006 | Graham | A61M 5/1415 5/503.1 |
| 2006/0075558 A1 * | 4/2006 | Lambarth | A61G 1/0212 296/20 |
| 2011/0277240 A1 | 11/2011 | Tijanic et al. | |
| 2012/0241571 A1 | 9/2012 | Masionis et al. | |
| 2016/0324701 A1 | 11/2016 | Cambridge et al. | |
| 2017/0246059 A1 | 8/2017 | Chinn | |
| 2021/0007920 A1 | 1/2021 | Zerhusen et al. | |
| 2021/0113394 A1 | 4/2021 | Xu et al. | |
| 2021/0186781 A1 | 6/2021 | Souke et al. | |

FOREIGN PATENT DOCUMENTS

| | | |
|---|---|---|
| WO | 2021072549 A1 | 4/2021 |
| WO | 2021168586 A1 | 9/2021 |

* cited by examiner

PATIENT SUPPORT APPARATUS WITH SUPPORT ASSEMBLY FOR MEDICAL DEVICE

CROSS-REFERENCE TO RELATED APPLICATION

This application claims priority to and the benefit of U.S. Provisional Patent Application No. 63/165,382, filed on Mar. 24, 2021, the disclosure of which is hereby incorporated by reference in its entirety.

BACKGROUND

Patient support systems facilitate care of patients in a health care setting. Patient support systems comprise patient support apparatuses such as, for example, hospital beds, stretchers, cots, tables, wheelchairs, and chairs. In certain situations (such as first response scenarios) caregivers must travel to the patient and transport the patient back to an emergency medical facility. Depending on the scenario, caregivers may also require the use of medical equipment (e.g. a heart monitor, defibrillator, and the like) to facilitate the care of the patient. Here, the medical equipment typically is separate from the patient support apparatus. The separate nature of the patient support apparatus and the medical equipment requires the caregivers to expend effort and attention to associate the equipment with the patient supported on the patient support apparatus. A dangerous situation could arise during transport if the medical equipment is not properly secured. Thus, there remains an opportunity to improve the coordination of the patient support apparatus and medical equipment.

SUMMARY

The present disclosure provides a patient support apparatus for concurrently transporting a patient and a medical device is provided. The patient support apparatus includes a base arranged for movement along floor surfaces and an intermediate frame coupled to the base and defining a patient support deck for supporting a patient. The patient support apparatus also includes a support assembly coupled to the intermediate frame for supporting the medical device for concurrent movement with the patient support apparatus. The support assembly includes a track operatively attached to the intermediate frame and extending between a first track end and a second track end with at least one curvilinear region defined therebetween. The support assembly also includes a mount configured to support the medical device and a carrier supporting the mount and coupled to the track for selective movement about the track between the first track end and the second track end. The support assembly further includes a retainer operatively attached to the carrier. The retainer includes a user interface, with the retainer being operable between an engaged state and a disengaged state. When the retainer is in the engaged state, the retainer inhibits relative movement of the carrier along the track between the first track end and the second track end. When the retainer is in the disengaged state, the retainer permits movement of the carrier along the track between the first track end and the second track end. The retainer moves from the engaged state to the disengaged state in response to user engagement with the user interface.

Any of the above aspects can be combined in full or in part. Any features of the above aspects can be combined in full or in part.

BRIEF DESCRIPTION OF THE DRAWINGS

Advantages of the present disclosure will be readily appreciated as the same becomes better understood by reference to the following detailed description when considered in connection with the accompanying drawings.

DETAILED DESCRIPTION

Figure 1A:
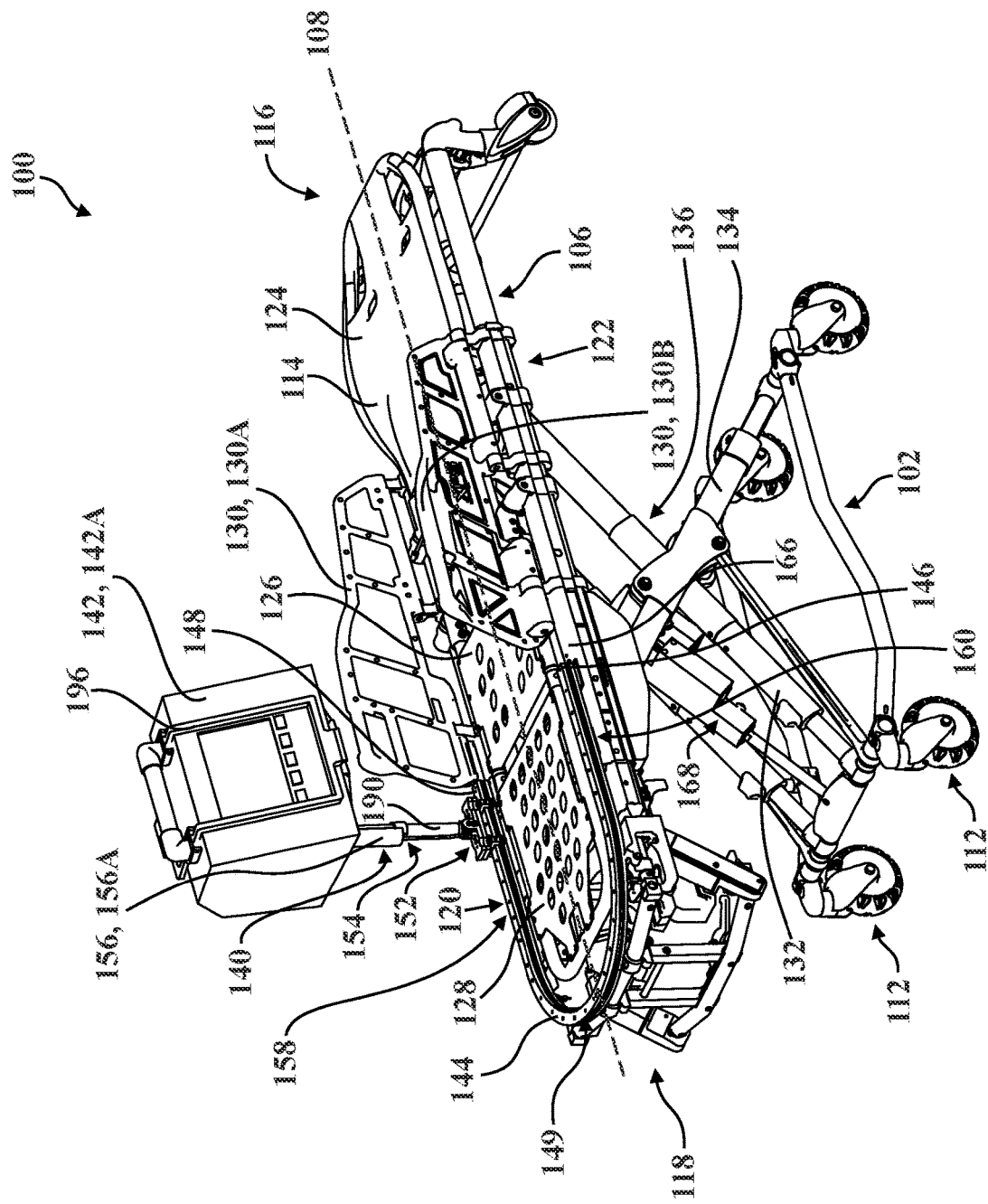
FIG. 1A is a perspective view of a patient support apparatus showing a support assembly with a carrier positioned at a second linear region of a track and locating a monitor facing towards a first linear region of the track.

Referring to FIGS. 1A-1C, 2A, and 2B, a patient support apparatus 100 is illustrated. The patient support apparatus 100 facilitates transportation of a patient in a health care and/or transportation setting. The patient support apparatus 100 illustrated in FIGS. 1A-1C, 2A, and 2B is realized as a cot. In other versions, however, the patient support apparatus 100 may be a hospital bed, a stretcher, a wheel chair, a stair chair, an evacuation, chair, and/or a similar apparatus utilized in the transportation and/or care of a patient. Other configurations are contemplated.

As shown in FIGS. 1A-1C, 2A, and 2B, the patient support apparatus 100 generally includes base 102 arranged for movement along floor surfaces. A lift mechanism 104 may couple to the base 102 to an intermediate frame 106. The base 102 may include two opposing lateral base sides coupled to two opposing longitudinal base sides. The longitudinal base sides may include longitudinally-extending rails 108 and the lateral base sides may include crosswise-extending rails 110 which may be coupled at the ends thereof to the rails longitudinally-extending rails.

The base 102 may further include a plurality of caster wheel assemblies 112 operatively connected adjacent to each corner of the base 102 defined by the longitudinally-extending rails 108 and the crosswise-extending rails 110. As such, the patient support apparatus 100 of FIGS. 1A-1C, 2A, and 2B may include four caster wheel assemblies 112. The wheel assemblies 112 may be configured to swivel to facilitate turning of the patient support apparatus 100. The wheel assemblies 112 may include a swivel locking mechanism to prevent the wheel assemblies 112 from swiveling when engaged. The wheel assemblies 112 may also include wheel brakes to prevent rotation of the wheel.

The patient support apparatus 100 includes an intermediate frame 106 coupled to the base 102 and defining a patient support deck 114 for supporting a patient. The intermediate frame 106 can be like that shown in U.S. Pat. No. 10,987,268 B2, which claims priority to U.S. Provisional Patent App. No. 62/488,441, filed on Apr. 21, 2017, entitled, "Emergency Cot with A Litter Height Adjustment Mechanism," the disclosures of which are hereby incorporated by reference in their entirety.

The intermediate frame 106 may extend longitudinally along a longitudinal axis 108 between a head end 116 and a foot end 118. The intermediate frame 106 may further extend laterally along a lateral axis (not shown in detail) between a left side 120 and a right side 122. The left side 120 and right side 122 may also be generally referred to as the first side and the second side, respectively. The intermediate frame 106 may be coupled to a variety of components that aid in supporting and/or transporting the patient. The patient support deck 114 may be defined by one or more articulable deck sections, for example, a fowler deck section 124, a seat deck section 126, and a leg deck section 128 to facilitate care and/or transportation of the patient in various patient positions.

The intermediate frame 106 may also be coupled to a pair of opposing lateral siderails 130 or side boards. More specifically, a left siderail 130A coupled to the left side 120 of the intermediate frame 106 and a right siderail 130B may be coupled to a right side 122 of the intermediate frame 106. The siderails 130 extend from opposing sides of the intermediate frame 106 and provide egress barriers for the patient on the patient support deck 114. The siderails 130 may also be utilized by an individual, such as a caregiver, an emergency medical technician (EMT), or another medical professional, to move or manipulate the patient support apparatus 100. In some versions, the siderails 130 may include a hinge, pivot, or similar mechanism to allow the siderails 130 to be folded or stored adjacent to or below the patient support deck 114.

One of the siderails 130A, 130B may be disposed along one of the lateral sides and the other one of the siderails 130A, 130B may be disposed along the other one of the lateral sides. More specifically, a left siderail 130A may be coupled to the left side 120 of the intermediate frame 106 and a right siderail 130B may be coupled to a right side 122 of the intermediate frame 106. The pair of siderails 130 may be configured to retain the patient between the siderails 130 on the patient support deck 114. More specifically, the patient may be positioned between the pair of siderails 130, with the pair of siderails 130 engaging the patient to prevent inadvertent movement of the patient laterally off of the patient support deck 114 (e.g., during transport).

The patient support apparatus 100 may also include the lift mechanism 104 interposed between the base 102 and the intermediate frame 106. The lift mechanism 104 may be configured to move between a plurality of vertical configurations including one or more extended configurations, where the intermediate frame 106 is elevated relative to the base 102, as shown in FIG. 1A, and one or more retracted configurations (e.g., a maximum lowered configuration; not shown) where the intermediate frame 106 is lowered such that it is in closer proximity to the base 102. The lift mechanism 104 can be like that shown in the U.S. Pat. No. 10,987,268 B2, previously referenced. However, other configurations are contemplated.

While moving between the plurality of vertical configurations, the lift mechanism 104 may move either the base 102 or the intermediate frame 106 relative to the other of the intermediate frame 106 or the base 102 depending on how the patient support apparatus 100 is supported during use. For example, the patient support apparatus 100 may be supported at the intermediate frame 106 when the patient support apparatus 100 is being unloaded/loaded into an emergency response vehicle (not shown) and the patient support apparatus 100 may be supported at the base 102 when the patient support apparatus 100 is resting on a surface. In instances where the patient support apparatus 100 is supported at the intermediate frame 106, the lift mechanism 104, while moving between the plurality of vertical configurations, moves the base 102 relative to the intermediate frame 106. In instances where the patient support apparatus 100 is supported at the base 102, the lift mechanism 104, while moving between the plurality of vertical configurations, moves the intermediate frame 106 relative to the base 102.

The pair of siderails 130 may be pivotable independently of one another between respective first and second positions. As such, one of the pair of siderails 130 may be in the second position to permit ingress/egress of the patient to the patient support deck 114, while the other one of the pair of siderails 130 may be in the first position, which may engage the patient after the patient is placed on the patient support deck 114 (e.g., the other siderails 130 in the first position extends the patient support deck 114 and may present a stop to prevent accidentally pushing the patient off of the patient support deck 114.) However, the pair of siderails 130 may both be simultaneously disposed in either of the first or second positions, and/or to various positions therebetween. In some versions, adjustment of the pair of siderails 130 between the positions may be employed to accommodate patients of different body types or sizes (e.g., bariatric patients). Other configurations are contemplated.

The lift mechanism 104 includes a first frame member 132 and a second frame member 134, both of which are coupled to the intermediate frame 106 and the base 102. A first end of the second frame member 134 may be pivotally coupled to the head end 116 of the intermediate frame 106 at a connection point such that the second frame member 134 may pivot about the connection point. A second end of the second frame member 134 may be pivotally coupled to a foot end 118 of the base 102 at a connection point such that the second frame member 134 may pivot about the connection point. Furthermore, a first end of the first frame member 132 may be pivotally coupled to a foot end 118 of the intermediate frame 106 via a slidable member.

As such, the first frame member 132 is pivotally coupled to the intermediate frame 106 and may pivot about the slidable member. Also shown, a second end of the first frame member 132 may be pivotally coupled to a head-end of the base 102 at a connection point such that the first frame member 132 may pivot about the connection point. Furthermore, the first frame member 132 and the second frame member 134 may be pivotally coupled to each other at the pivot axle to form an "X" frame 136.

The lift mechanism 104 may include a second, similarly constructed X frame 136, which may include a third frame member and a fourth frame member. Similar to X frame 136, the third frame member and the fourth frame member may be pivotally coupled to a side of the intermediate frame 106 and a side of the base 102. For example, the third frame member and the fourth frame member of X frame 136 may be pivotally coupled to a side of the intermediate frame 106 and a side of the base 102, which oppose a side of the intermediate frame 106 and a side of the base 102 to which the first frame member 132 and the second frame member 134 are coupled. It will be appreciated that any reference herein to the first frame member 132 may also be a reference to the third frame member. Similarly, any reference to the second frame member 134 may also be a reference to the fourth frame member.

In FIGS. 1A-1C, 2A, and 2B, the frame members 132, 134 are hollow and telescopingly include further frame members. The further frame members may be supported for movement into and out of the respective frame members 132, 134 to extend a length of the respective frame members 132, 134. In the version shown in 1A-1C, 2A, and 2B, the further frame members extend out of frame members 132, 134 toward the base 102. However, in other examples, the further frame members may extend out of frame members 132, 134 toward the intermediate frame 106. In these examples, frame members 132, 134 are coupled to the base 102 or the intermediate frame 106 via further frame members. However, in other examples, the frame members 132, 134 may be of a fixed length and exclude further frame members. Additionally, while the lift mechanism 104 of the representative version illustrated in 1A-1C, 2A, and 2B includes four frame members 132, 134 the lift mechanism 104 may include any suitable number of frame members.

Those having ordinary skill in the art will appreciate that the lift mechanism 104 may move between the plurality of vertical configurations due to a patient care provider applying a manual action to the lift mechanism 104, or components thereof. Additionally, or alternatively, the patient support apparatus 100 may include one or more actuators 138, which may be coupled to any suitable component of the lift mechanism 104 and may be configured to move the lift mechanism 104 between the plurality of vertical configurations. As shown in FIG. 1A, the illustrated actuator 138 is realized as a hydraulic linear actuator, which is connected to and extends between the base 102 and the intermediate frame 106. In this particular version, the hydraulic linear actuator includes a cylindrical housing fastened to intermediate frame 106, the cylindrical housing including a reciprocal rod having a piston (not shown) located within the cylindrical housing. The distal end of the reciprocal rod is connected by a joint to the base 102. The joint allows pivotal movement about two orthogonally related axes. Extension and retraction of the reciprocal rod will facilitate movement of the frame members of the lift mechanism 104 about the axis of the reciprocal rod.

The actuator 138 is further described in U.S. Pat. No. 7,398,571, filed on Jun. 30, 2005, entitled, "Ambulance Cot and Hydraulic Elevating Mechanism Therefor," the disclosure of which is hereby incorporated by reference in its entirety. Furthermore, techniques for utilizing actuator 138 to manipulate the components of the patient support apparatus 100 can be like those described in U.S. Pat. No. 10,987,268 B2, previously referenced. Other configurations are contemplated.

In some versions, the actuator 138 may not be the hydraulic linear actuator shown in FIG. 1A. The actuator 138 may be any actuator suitable for actuating the lift mechanism 104 such that the lift mechanism 104 moves between the plurality of vertical configurations. For example, the actuator 138 may be an electric motor, a servo motor, a pneumatic actuator, or any other suitable actuator.

As shown throughout FIGS. 1A-1C and 2A-2B, the patient support apparatus 100 also includes a support assembly 140 coupled to the intermediate frame 106 for supporting a medical device 142 for concurrent movement with the patient support apparatus 100. More specifically, and as is described in greater detail below, the medical device 142 moves concurrently with the patient support apparatus 100 because the support assembly 140 supports the medical device 142 while the support assembly 140 is coupled to the patient support apparatus 100 via the intermediate frame 106. The illustrated medical device 142 may be realized as a heart monitor, an automated defibrillator (AED), or any other suitable type of medical device 142 utilized in connection with patient care.

Figure 3A:
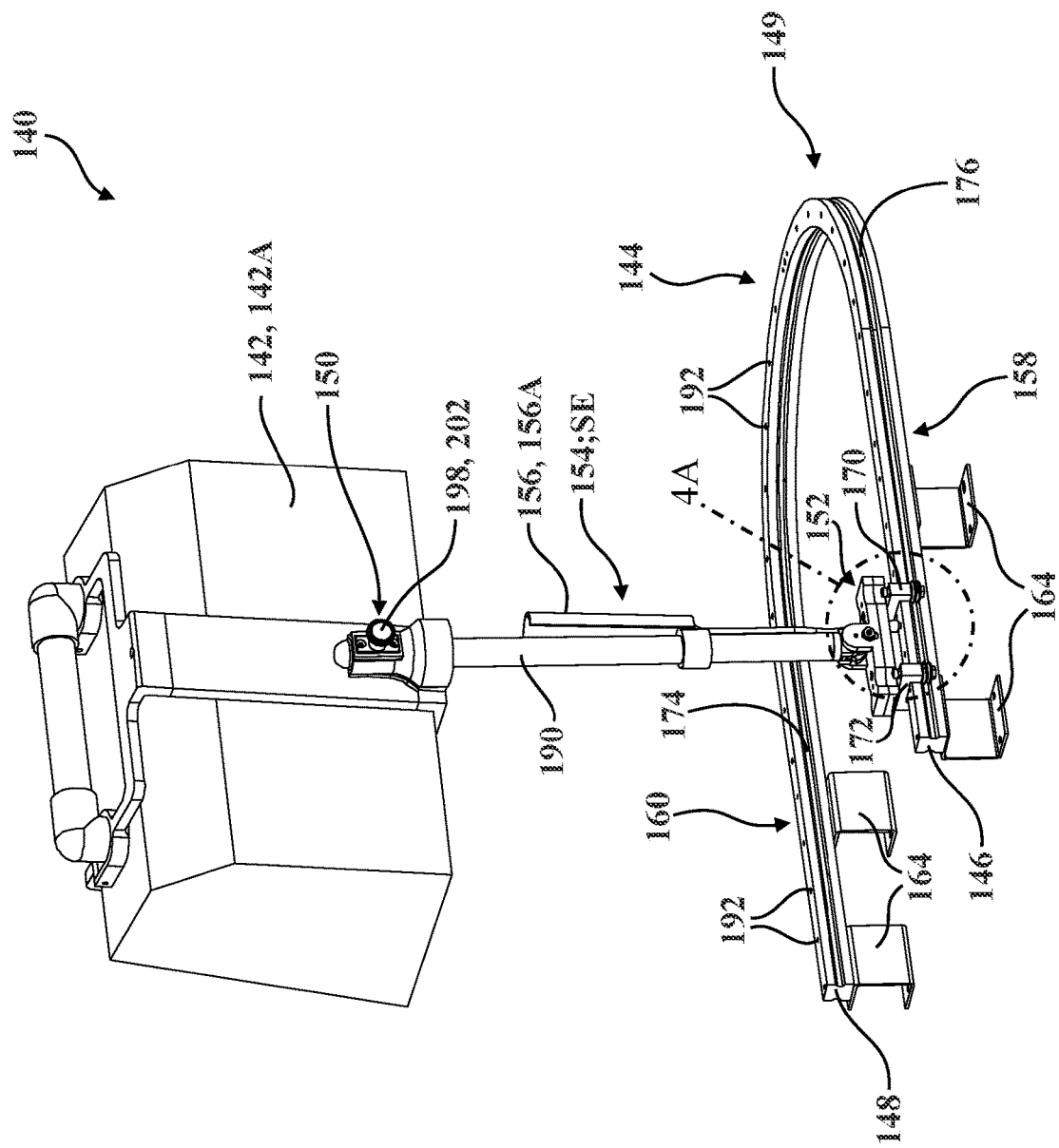
FIG. 3A is a perspective view of the support assembly with a user interface handle in a rest position and a pin in a first pin position disposed within an aperture of the track.
Figure 3B:
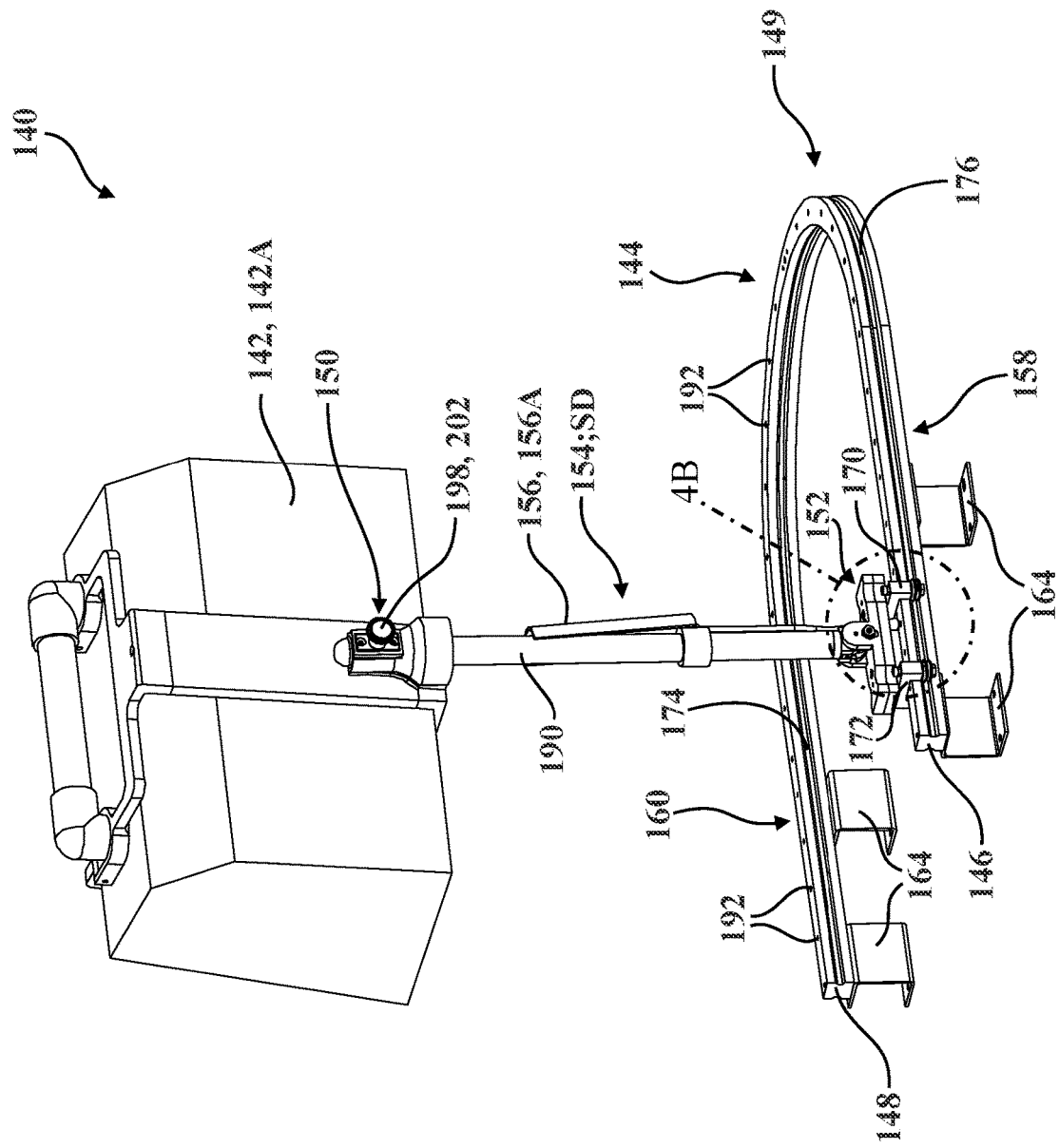
FIG. 3B is a perspective view of the support assembly with the user interface handle in an activated position and the pin in a second pin position spaced from the aperture of the track.
Figure 3C:
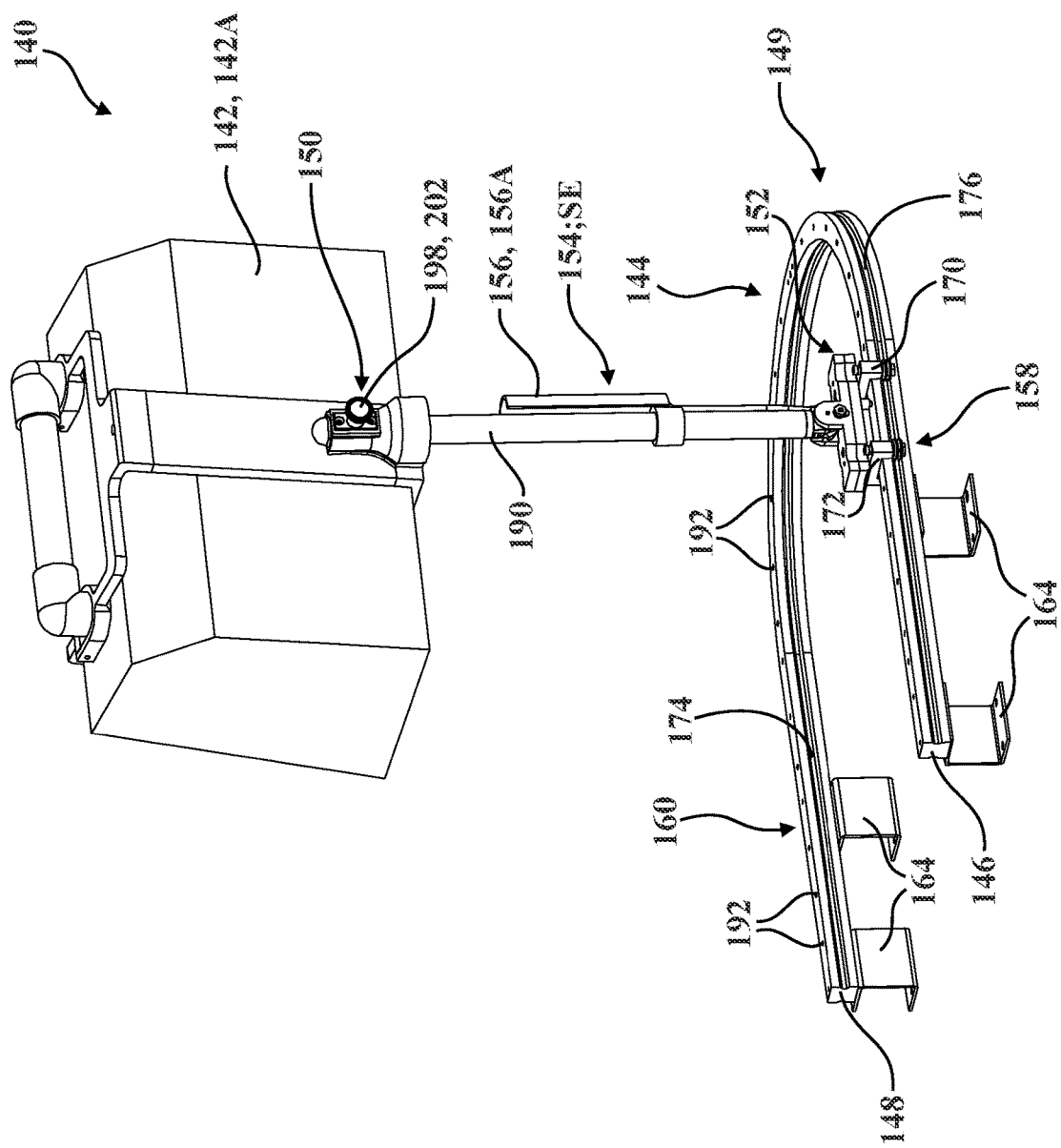
FIG. 3C is another perspective view of the support assembly with the user interface handle in the activated position and the pin in the first pin position disposed within another aperture of the track.

The support assembly 140 includes a track 144 operatively attached to the intermediate frame 106 and extending between a first track end 146 and a second track end 148. At least one curvilinear region 149 is defined between the first and second track ends 146, 148. As best shown in FIGS. 3A-3C, the support assembly 140 also includes a mount 150 configured to support the medical device 142. The support assembly 140 further includes a carrier 152 supporting the mount 150 and coupled to the track 144 for selective movement between the first and second track ends 146, 148 as described in greater detail below.

The support assembly 140 also include a retainer 154 operatively attached to the carrier 152. The retainer 154 is operable between an engaged state SE and disengaged state SD. In the engaged state SE (see FIGS. 3A and 4A; see also FIG. 3C), the retainer 154 inhibits relative movement of the carrier 152 along the track 144 between the first track end 146 and the second track end 148. In the disengaged state SD (see FIGS. 3B and 4B), the retainer 154 permits movement of the carrier 152 along the track 144 between the first track end 146 and the second track end 148. In other words, the carrier 152 is able to be positioned about the track 144 when the retainer 154 is in the disengaged state SD and is maintained in its current position when the retainer 154 is in the engaged state SE. The retainer 154 also includes a user interface 156 that is responsive to a user (e.g., a caregiver) to move the retainer 154 between the engaged state SE and the disengaged state SD.

The track 144 is configured to allow the carrier 152 to travel along at least a portion the left and/or right sides 120, 122 of the intermediate frame 106. Put differently, in the illustrated version, the first track end 146 is arranged adjacent to the right side 122 of the intermediate frame 106, and the second track end 148 arranged adjacent to the left side 120 of the intermediate frame 106. However, other arrangements are contemplated, such as with the first track end 146 arranged adjacent to the left side 120 and with the second track end 148 arranged adjacent to the right side 122. The track 144 may define a first linear region 158 adjacent to the first track end 146, and a second linear region 160 adjacent to the second track end 148. In some versions, the first and second linear regions 158, 160 are substantially parallel to each other and are spaced laterally from each other. In the illustrated versions shown in FIGS. 1A-3, the track 144 has a generally U-shaped profile with a single curvilinear region 149, and includes substantially parallel and laterally spaced first and second linear regions 158, 160. However, other configurations are contemplated.

In some versions, and as is best shown in FIG. 3, the support assembly 140 may include a plurality of brackets 164 for coupling to intermediate frame rails 166 on the first and second sides 120, 122 at the foot end 118 of the patient support apparatus 100. The plurality of brackets 164 facilitate assembly to the patient support apparatus 100, such as via bolts, rivets, or other fasteners, as well as by other attachment methodologies (e.g., welding). However, those having ordinary skill in the art will appreciate that other attachment mechanisms may also be used for coupling the support assembly 140 to the intermediate frame 106. For example, the track 144 may be directly bolted or welded to the intermediate frame rails 166 without the use of the plurality of brackets 164. Other configurations are contemplated.

The carrier 152 includes a plurality of rollers 168 arranged to engage the track 144 for selective movement between the first and second track ends 146, 148. As shown throughout FIGS. 3A, 3B, 4A, and 4B, the carrier 152 may include a first rail car 170 having at least one first car roller 168A disposed in sliding engagement with the track 144, and a second rail car 172 spaced from and coupled to the first rail car 170 and having at least one second car roller 168B disposed in sliding engagement with the track 144. In some versions, as best shown in FIGS. 3A and 3B, the first rail car 170 includes a pair of first car rollers 168A each disposed in sliding engagement with the track 144 and the second rail car 172 includes a pair of second car rollers 168B each disposed in sliding engagement with the track 144. Here, the track 144 may include or otherwise define an inward grove 174 and outward grove 176, with each grove 174, 176 engaging one of the two rollers 168 of the first and second pairs of car rollers 168A, 168B. However, other configurations are contemplated, and different arrangements of rollers, bushings, sliders, and the like may be utilized.

Figure 8:
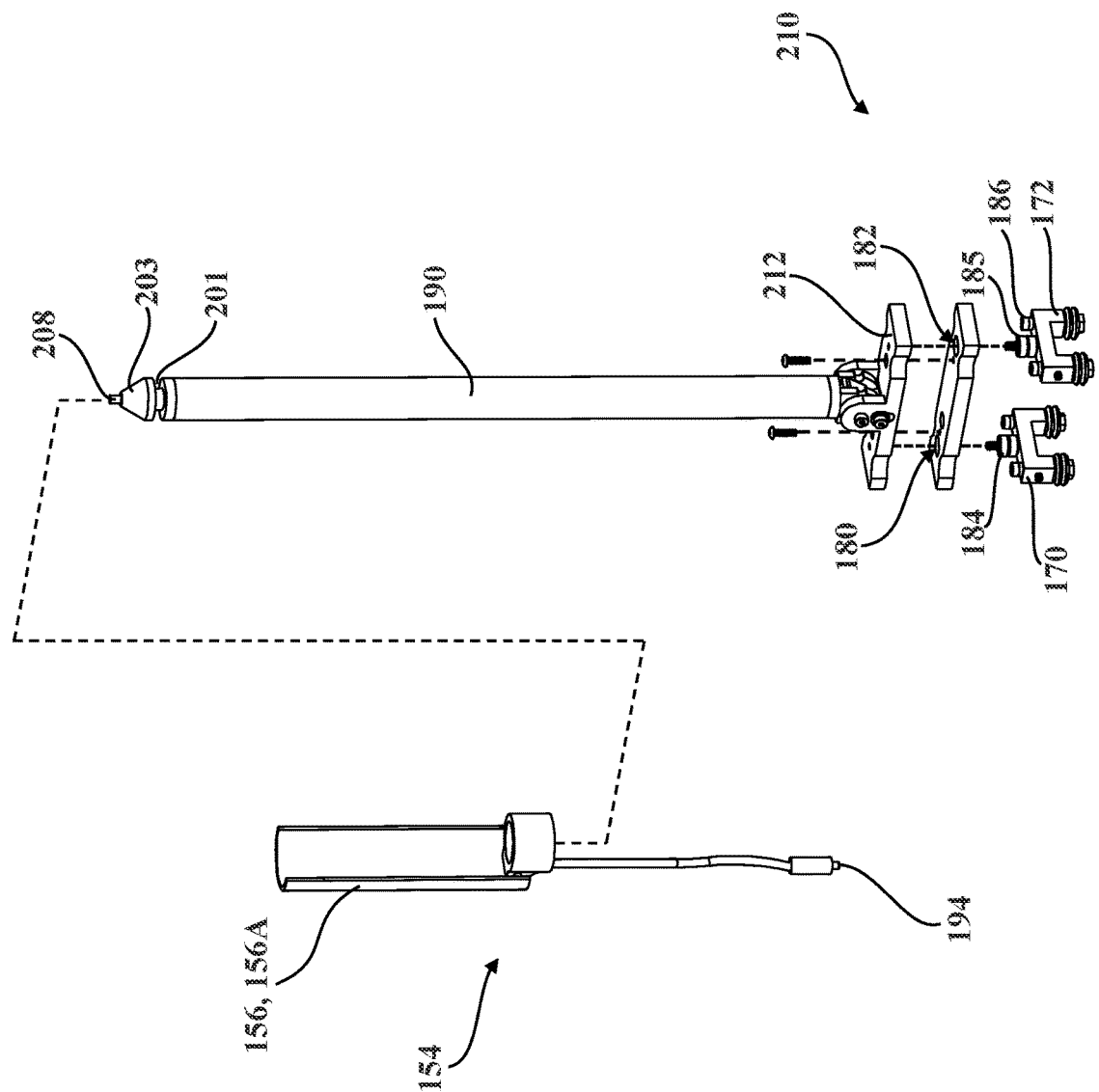
FIG. 8 is an exploded, perspective view of the retainer, a mount, an extension rod, and a carrier.

As best shown in FIG. 8, the carrier 152 may include a support plate 178 coupling the first and second rail cars 170, 172. Here, the support plate 178 supports the first and second rail cars 170, 172. Although the first and second rail cars 170, 172 are coupled with the support plate 178, the first rail car 170 is pivotably coupled to the support plate 178 about a first car axis CA1, and the second rail car 172 is pivotably coupled to the support plate 178 about a second car axis CA2 spaced from the first car axis CA1. In other words, the first and second rail cars 170, 172 are able to independently pivot relative to the support plate 178 about their own pivot axis CA1, CA2. To facilitate the independent pivoting movement of the first rail car 170, the support plate 178 may define a first seat 180 arranged about the first car axis CA1 with a first bearing 184 at least partially disposed in the first seat 180. Similarly, to facilitate the independent pivoting movement of the second rail car 172, the support plate 178 may define a second seat 182 arranged about the second car axis CA2 with a second bearing 185 at least partially disposed in the second seat 182. The first and second bearings 184, 185 may be fully disposed in the first and second seats 180, 182, respectively. In some versions, an arrangement of bearings, bushings, and/or may be disposed in each of the first and second seats 180, 182. To control and limit the independent pivot movement of the first and second rail cars 170, 172, the first and second rail cars 170, 172 may define at least one limiter 186 extending from a top surface 188 of the first and second rail cars 170, 172. The limiters 186 function to limit the pivot movement of the define respective top surfaces 188 each facing the mount 150, with at least one limiter 186 extending from the top surface of the first and second rail cars 170, 172 for limiting the pivot motion of the first and second rail cars 170, 172. In some versions, such as shown in FIG. 8, the first and second rail cars 170, 172 each define two limiters 186 that extend from the top surface 188 of the respective rail cars 170, 172 about opposite sides of the support plate 178.

The support assembly 140 also includes an extension rod 190 coupling the mount 150 to the support plate 178 and extending between the carrier 152 and the retainer 154. As shown in FIGS. 1A-8, the extension rod 190 has a generally cylindrical profile. However, other geometric configurations could also be used for the extension rod 190. In the illustrated version, the extension rod 190 supports the user interface 156 of the retainer 154. In some versions, the user interface 156 includes a handle 156A that is mounted to the extension rod 190. The handle 156A enables the user to simultaneously engage the handle 156A to place the retainer 154 in the disengaged state SD and move the support assembly 140 along the track 144 between the ends 146, 148. In other words, when the user places their hand on and engages the handle 156A to position the retainer 154 in the disengaged state SD, the user is seamlessly able to physically move the support assembly 140 with the same hand that is engaged with the handle 156A. This convenient, one-handed operation allows the user to maintain focus on the patient while positioning the support assembly 140 with the goal of moving the medical device 142 to the desired location. FIG. 3A depicts the handle 156A in an released position with the retainer 154 in the engaged state SE, whereas FIG. 3B depicts the handle in a depressed position with the retainer 154 in the disengaged state SD. As shown in FIGS. 3A and 3B, the handle 156A is arranged relatively closer to the extension rod 190 in the depressed position (see FIG. 3B) compared to the proximity of the handle 156A to the extension rod 190 when the handle is in the released position (see FIG. 3B).

Figure 4A:
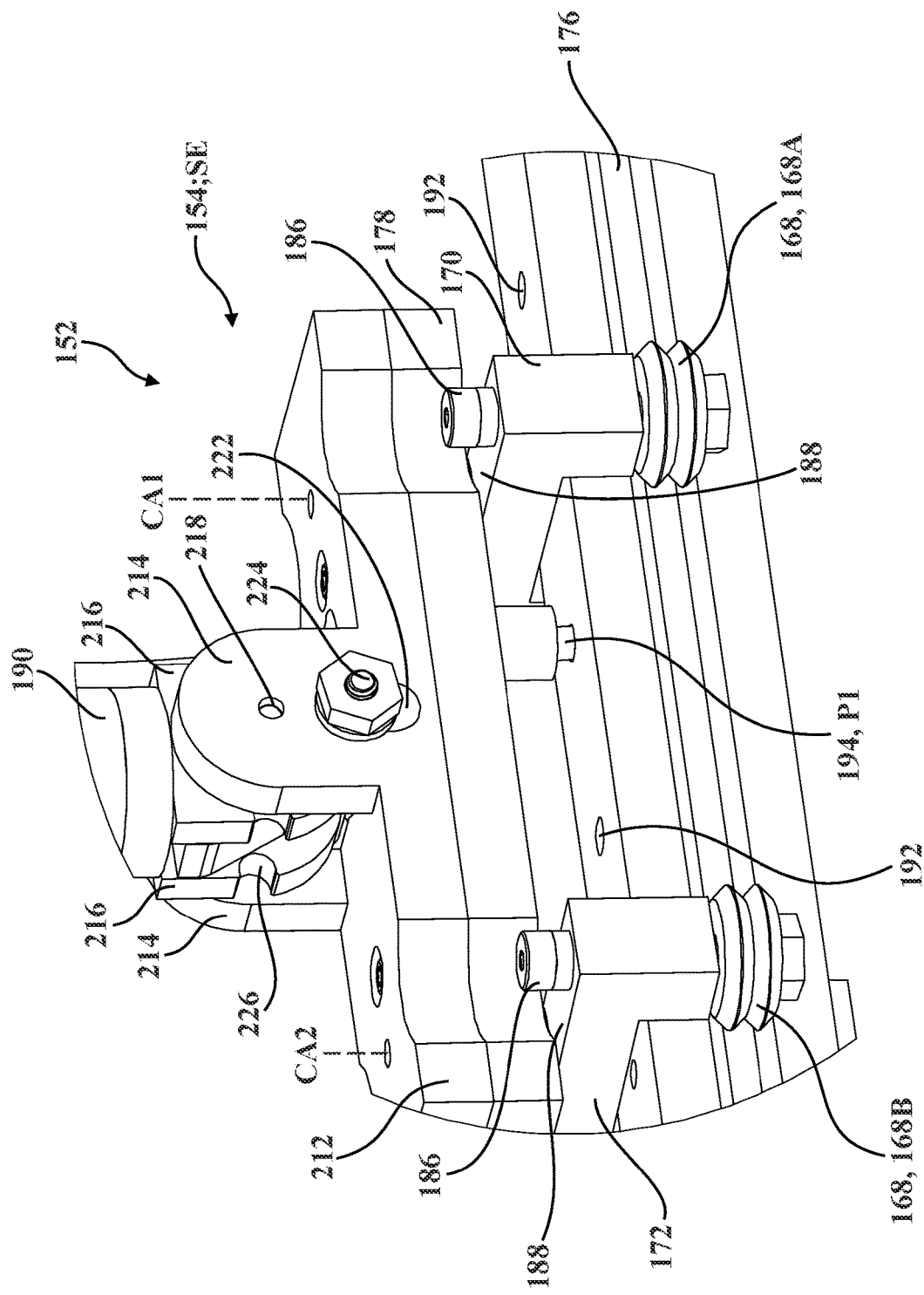
FIG. 4A is a partial enlarged perspective view of FIG. 3A with the pin in the first pin position disposed within the aperture of the track.
Figure 4B:
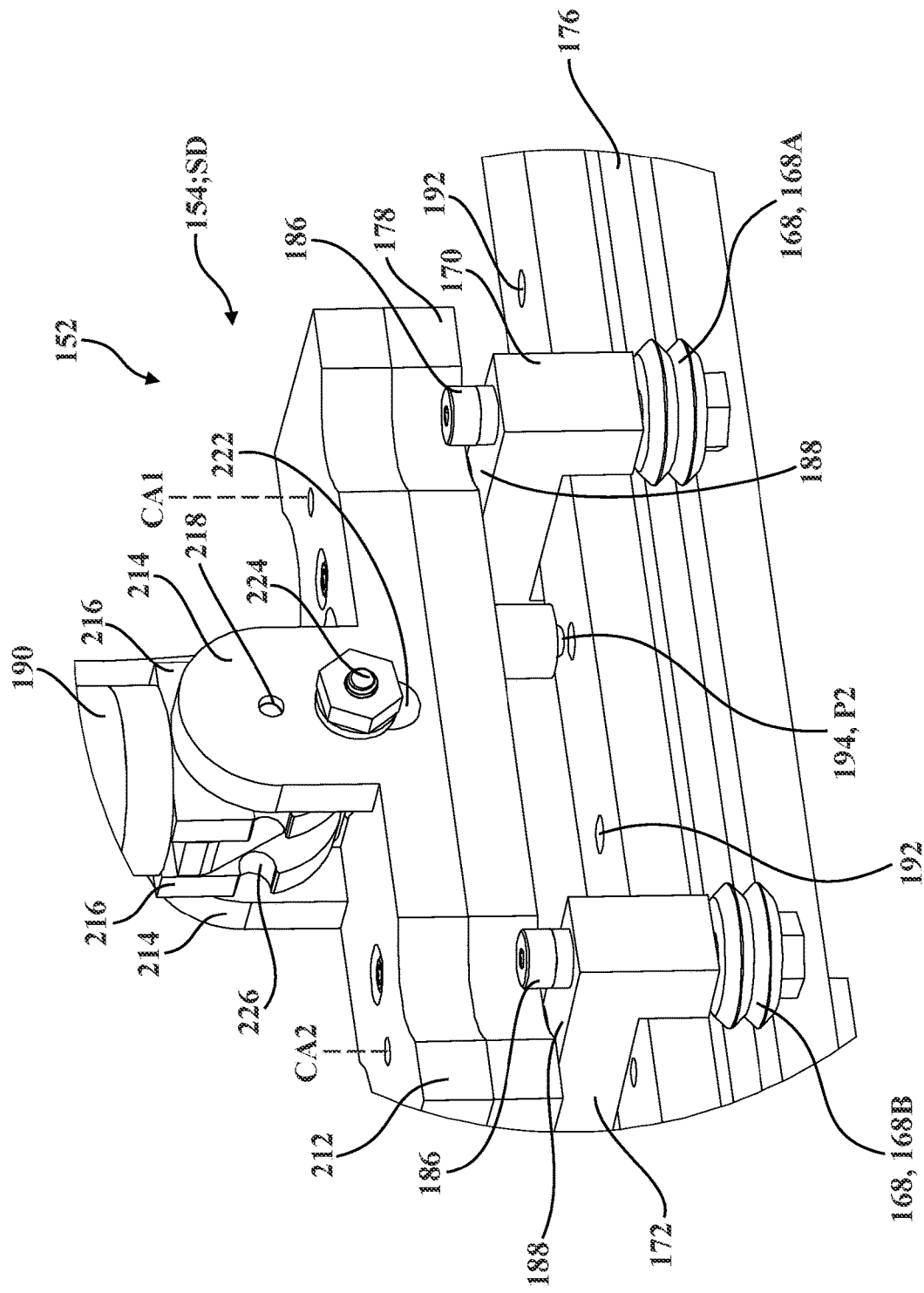
FIG. 4B is a partial enlarged perspective view of FIG. 3A with the pin in the second pin position spaced from the aperture of the track.
Figure 5:
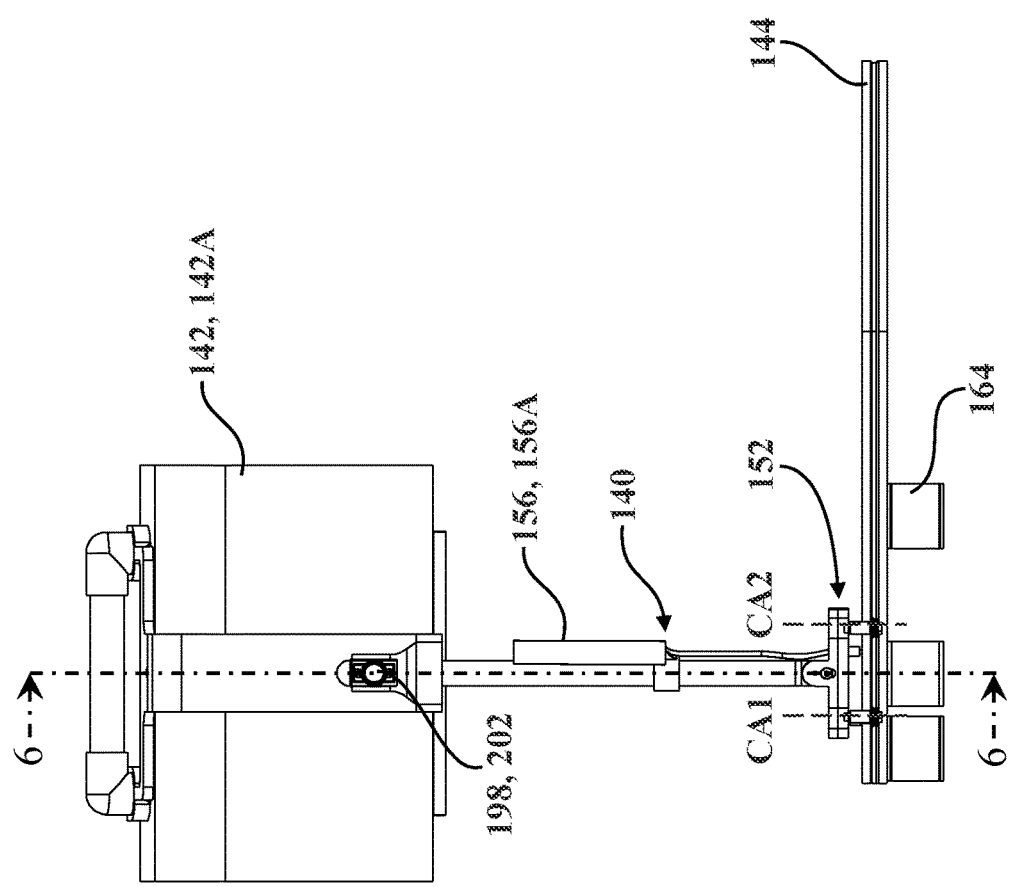
FIG. 5 is a side view of the support assembly.
Figure 6:
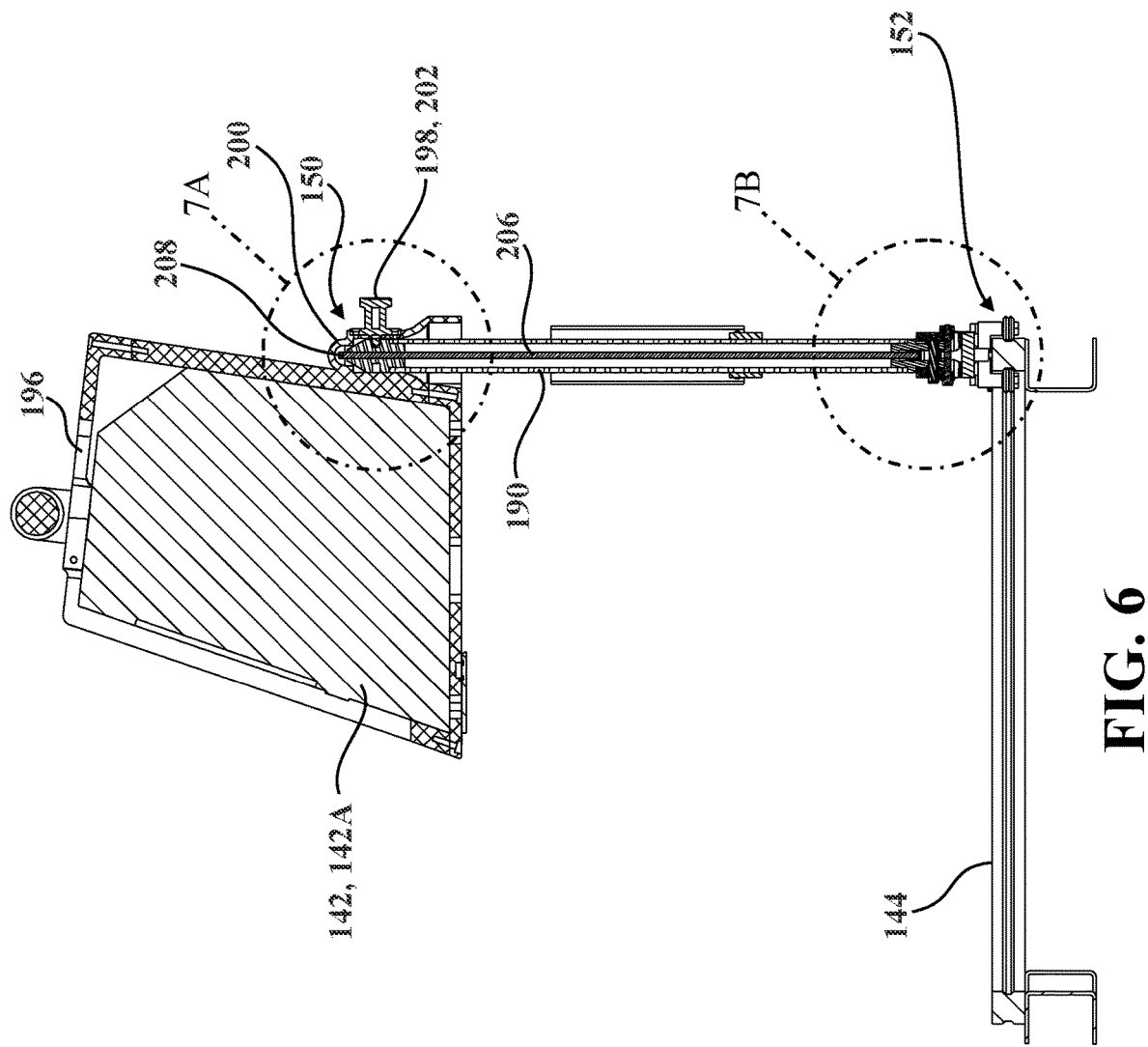
FIG. 6 is a cross-sectional view of the support assembly taken along the plane of FIG. 5.
Figure 7A:
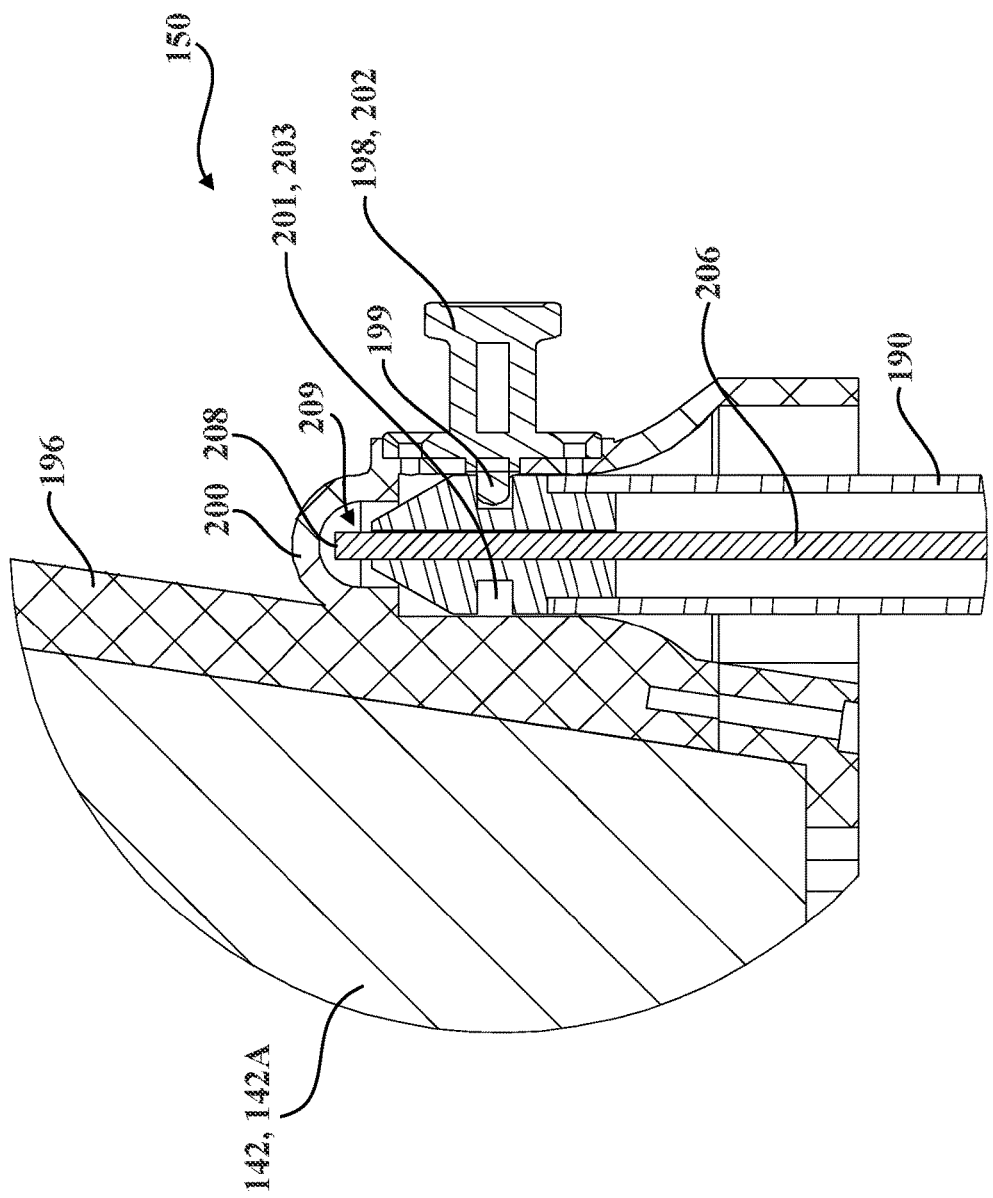
FIG. 7A is an enlarged partial cross-sectional view of the support assembly of FIG. 6 showing a mount engaged with an equipment frame and a receptacle coupled to the equipment frame and an activation mechanism for a pivot assembly shielded within the receptacle.
Figure 7B:
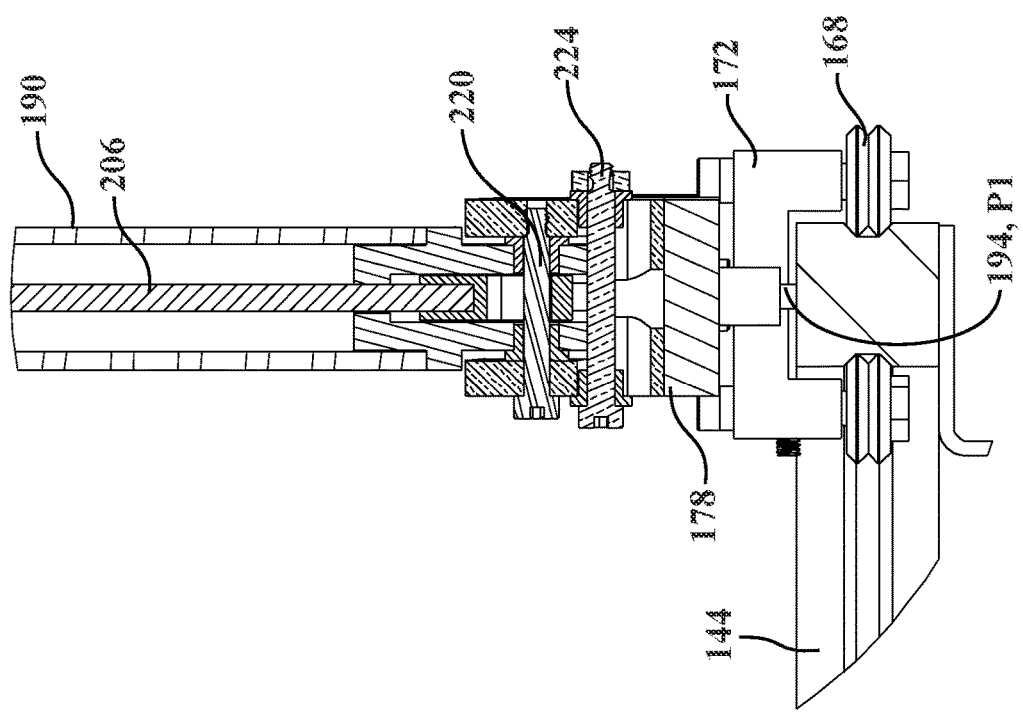
FIG. 7B is an enlarged partial cross-sectional view of the pivot mechanism.

As best shown in FIGS. 3A and 3B, the track 144 may define a plurality of apertures 192 at predefined positions between the first track end 146 and the second track end 148. The plurality of apertures 192 are arranged to receive a pin 194 supported by the carrier 152. The user interface 156 is used to move the pin between a first pin position P1 where the pin 194 is engaged in one of the plurality of apertures 192 and a second pin position P2 where the pin 194 is disengaged from the plurality of apertures 192. As best shown in FIGS. 3A and 4A, when the handle 156A is in the released position, the retainer 154 is in the engaged state SE and the pin 194 is in the first pin position P1 and is engaged with one of the plurality of apertures 192 such that the user is inhibited from moving the carrier 152 about the track 144. In FIGS. 3B and 4B, when the handle 156A is in the depressed position, the retainer 154 is in the disengaged state SD and the pin 194 is in the second pin position P2 disengaged from the plurality of apertures 192 such that the user is able to move the carrier 152 about the track 144 between the plurality of apertures 192. In some versions, the pin 194 or another portion of the retainer 154 may be provided with one or more biasing elements (not shown but generally known in the art) arranged to urge the pin 194 towards the first pin position P1. Here, it will be appreciated that the retainer 154 may include or otherwise be realized with push/pull cables, linkages, and the like to translate motion of the user interface 156 (e.g., the handle 156A) into corresponding movement of the pin 194. Other configurations are contemplated.

Figure 1B:
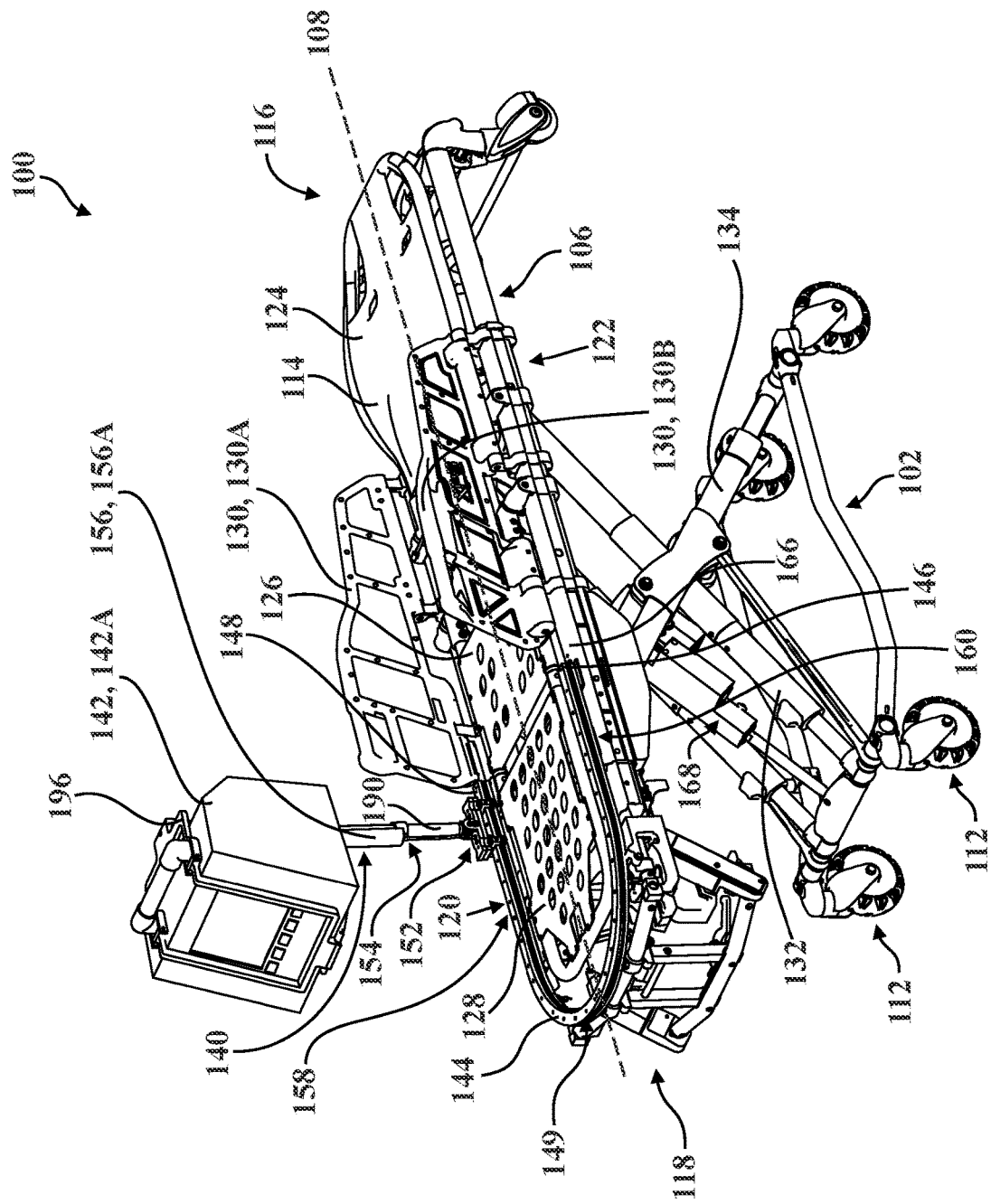
FIG. 1B is another perspective view of the patient support apparatus of FIG. 1A with the monitor facing towards a foot end of the patient support apparatus.

The patient support apparatus 100 may also include an equipment frame 196 for securing the medical device 142. The dimensions and configuration of the equipment frame 196 may generally correspond to the structural arrangement of the medical device 142 to be supported by the support assembly 140. For example, as shown in FIG. 1A, the equipment frame 196 is configured to support a monitor 142A. Other configurations are contemplated. As shown in FIG. 3A, a mount adjuster 198 may be provided to enable the medical device 142 (e.g. monitor) to be rotated about the extension rod 190 to position the medical device 142 in an orientation desired by the user. Exemplary rotational positions of the medical device 142 are illustrated in FIGS. 1A and 1B. In some versions, the mount adjuster 198 may include a plunger 199 that is disposed within a plunger catch 201 formed in a cap 203 of the mount 150 coupled to the extension rod 190 (see FIG. 7A). Here, the plunger catch 201 may define a plurality of discrete radial positions (not shown in detail) to releasably receive the plunger 199 of the mount adjuster 198 to define the rotational positions. In some versions, the plunger 199 may engage the plunger catch 201 in other ways, such as by interference or friction fit (e.g., without discrete radial positions formed in the plunger catch 201). Other configurations are contemplated. The mount adjuster 198 may be spring biased (not shown in detail) to urge the plunger 199 into engagement with the plunger catch 201.

In some versions, the equipment frame 196 includes a receptacle 200 coupled to the equipment frame 196 for releasably engaging the extension rod 190 (e.g., via engagement with the cap 203). Here, the receptacle 200 and the cap 203 have correspondingly-shaped profiles that help facilitate releasable attachment and selective rotational movement of the equipment frame 196 about the mount 150. In some versions, the mount 150 may also include a mount release 202 to facilitate the removal of the equipment frame 196 from the mount 150, such as to permit the medical device 142 to be separated from the patient support apparatus 100 (see FIG. 1C). In the illustrated version, engagement between the plunger 199 of the mount adjuster 198 and the plunger catch 201 formed in the cap 203 of the mount 150 also serves to prevent removal of the equipment frame 196 from the mount 150. Put differently, the mount adjuster 198 also serves as the mount release 202 in the illustrated version. However, it will be appreciated that separate devices could be employed to rotate and remove the equipment frame 196 about the mount 150.

Figure 1C:
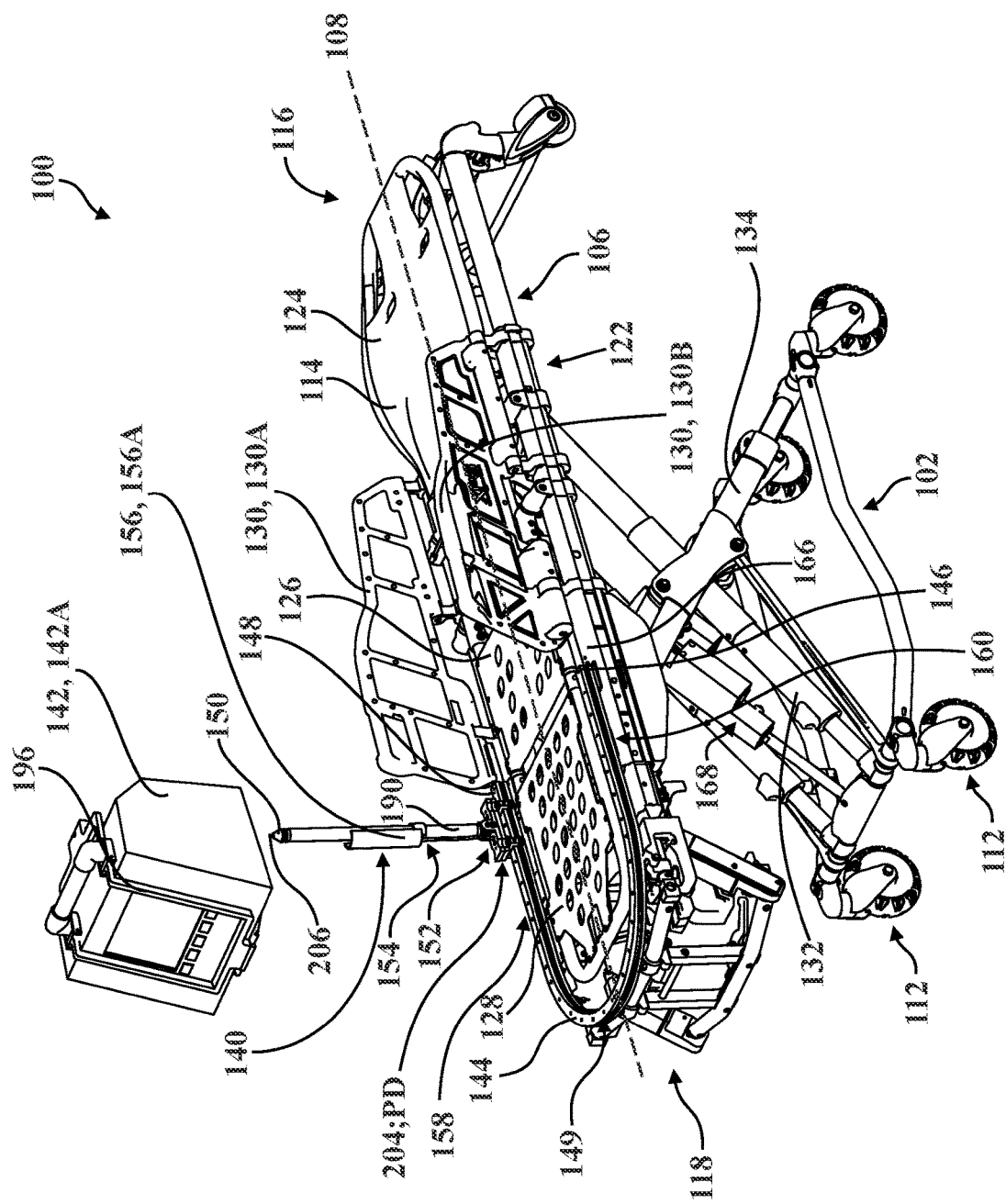
FIG. 1C is another perspective view of the patient support apparatus of FIG. 1A with the monitor disengaged from a mount.
Figure 1D:
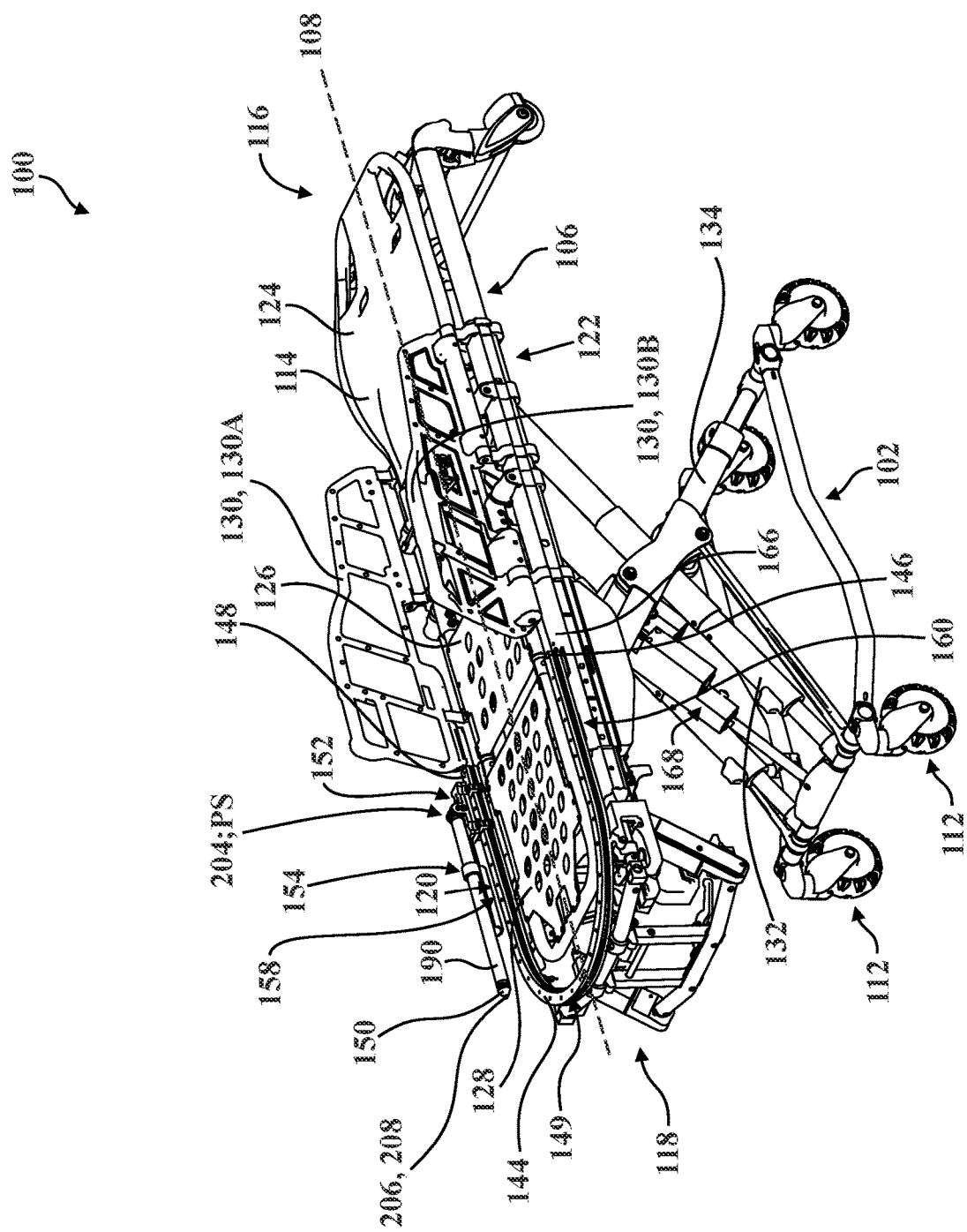
FIG. 1D is another perspective view of the patient support apparatus of FIG. 1A with the monitor disengaged from the mount and an extension rod in a stowed position.
Figure 2A:
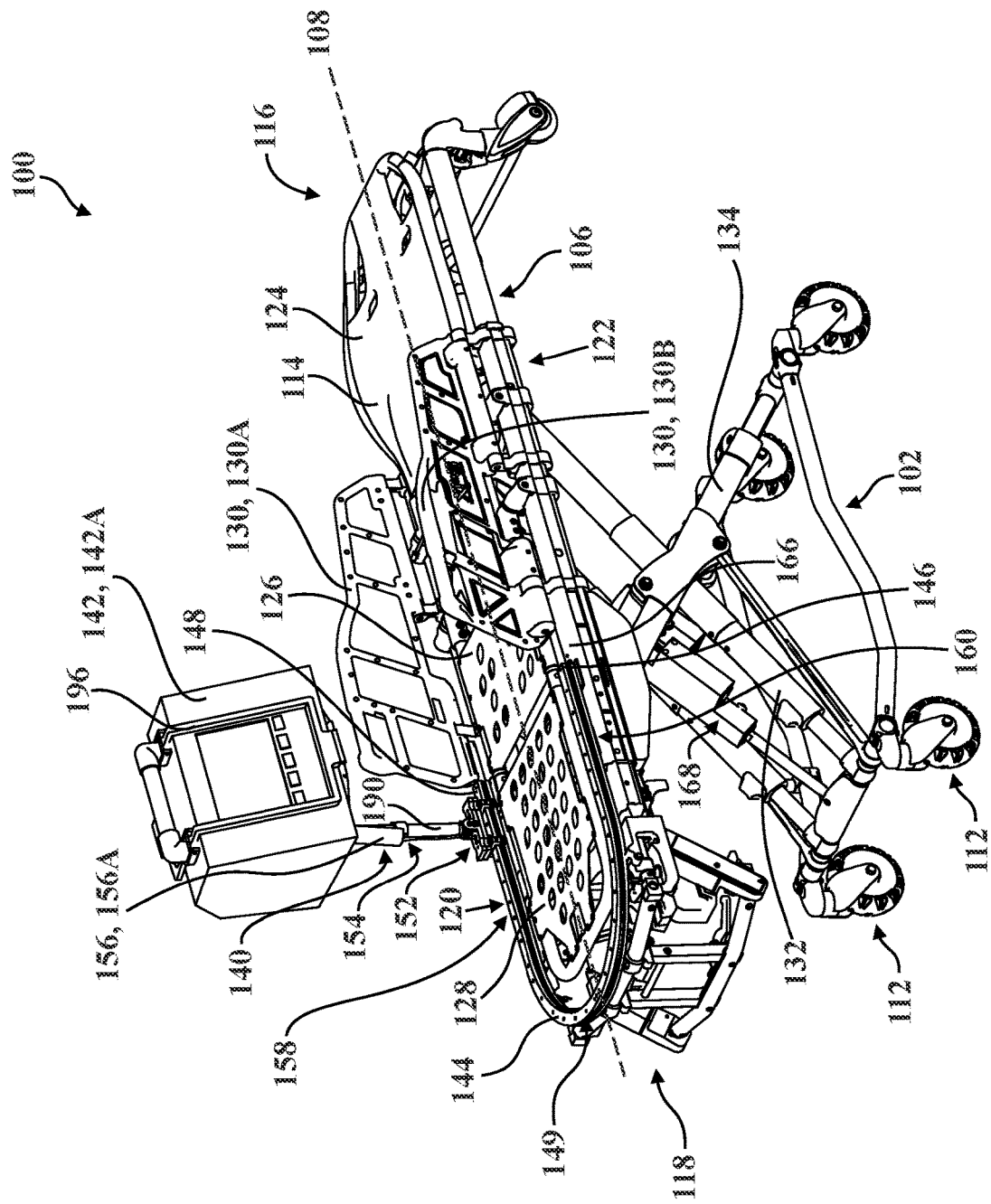
FIG. 2A is another perspective view of a patient support apparatus showing the support assembly with the carrier positioned at the second linear region of the track.
Figure 2B:
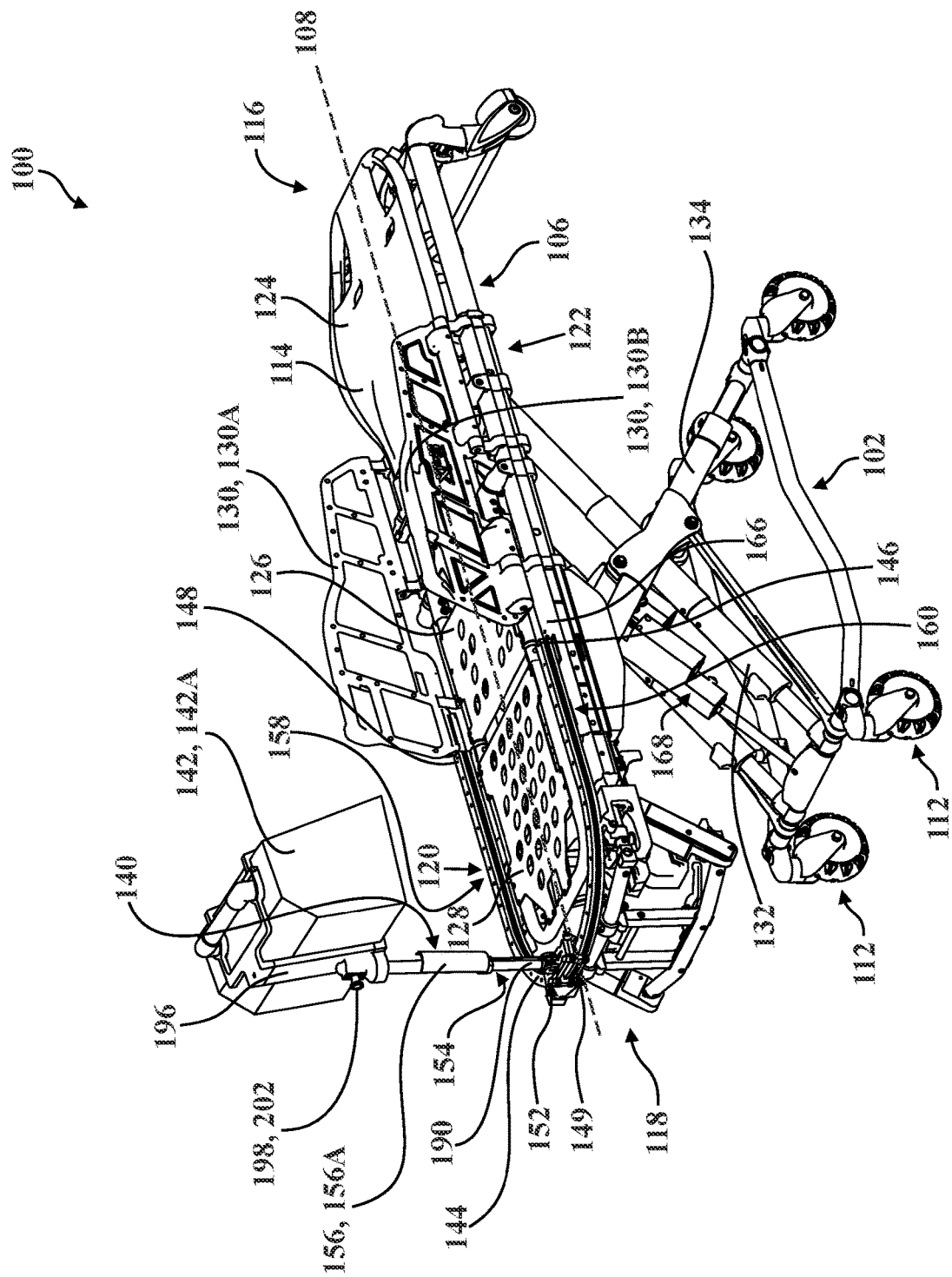
FIG. 2B is another perspective view of a patient support apparatus showing the support assembly with the carrier positioned at a curvilinear region of the track.

The patient support apparatus 100 may also include a pivot assembly 204 interposed between the extension rod 190 and the support plate 178 to permit selective movement between a deployed position PD (see FIG. 1C) and a stowed position (see FIG. 1D). In the deployed position PD, as illustrated in FIG. 1C (as well as in FIG. 1A-1B; not shown in detail), the extension rod 190 extends generally perpendicular to the support plate 178. In contrast, in the stowed position PS shown in FIG. 1D, the extension rod 190 extends generally horizontal relative to the support plate 178 and/or the intermediate frame 106. In some versions, the pivot assembly 204 includes a safety pin 206 extending from a pusher 207 arranged adjacent to the support plate 178, through the extension rod 190, to a distal end 208 located in a void 209 defined in the cap 203 of the mount 150. In this configuration, the pivot assembly 204 can only be moved when the distal end 208 of the safety pin 206 is pressed. However, because the distal end 208 of the safety pin 206 is located inside the receptacle 200 of the equipment frame 196, the distal end 208 is only accessible by the user when the equipment frame 196 has been removed from the mount 150. The shielded nature of the distal end 208 of the safety pin 206 ensures that the pivot assembly 204 only functions to pivot the extension rod 190 when the medical device 142 has been removed from the mount 150, thereby eliminating the possibility that the medical device 142 will pivot concurrently with the extension rod 190.

Figure 9A:
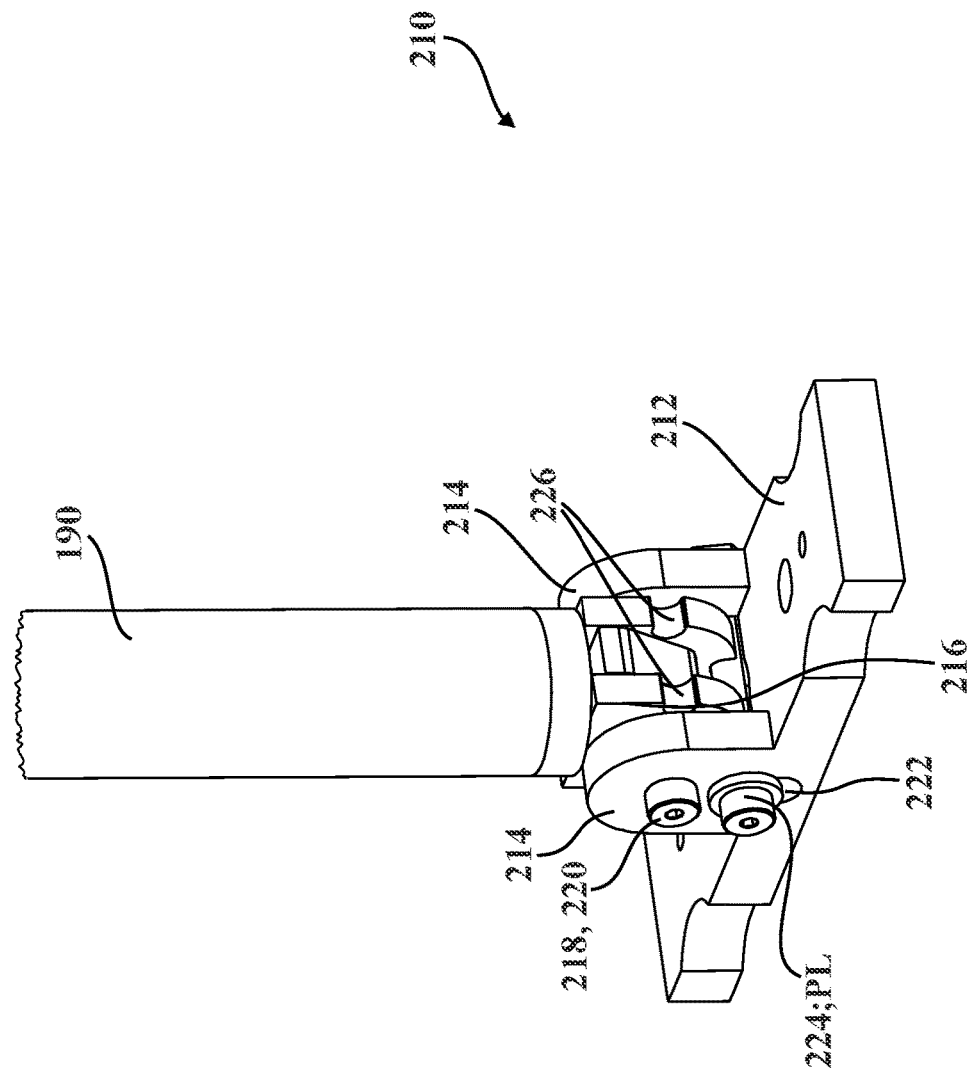
FIG. 9A is a perspective view of the pivot assembly with a safety pin in an inactivated state and a movable rod in a locked position to prevent operation of the pivot assembly.
Figure 9B:
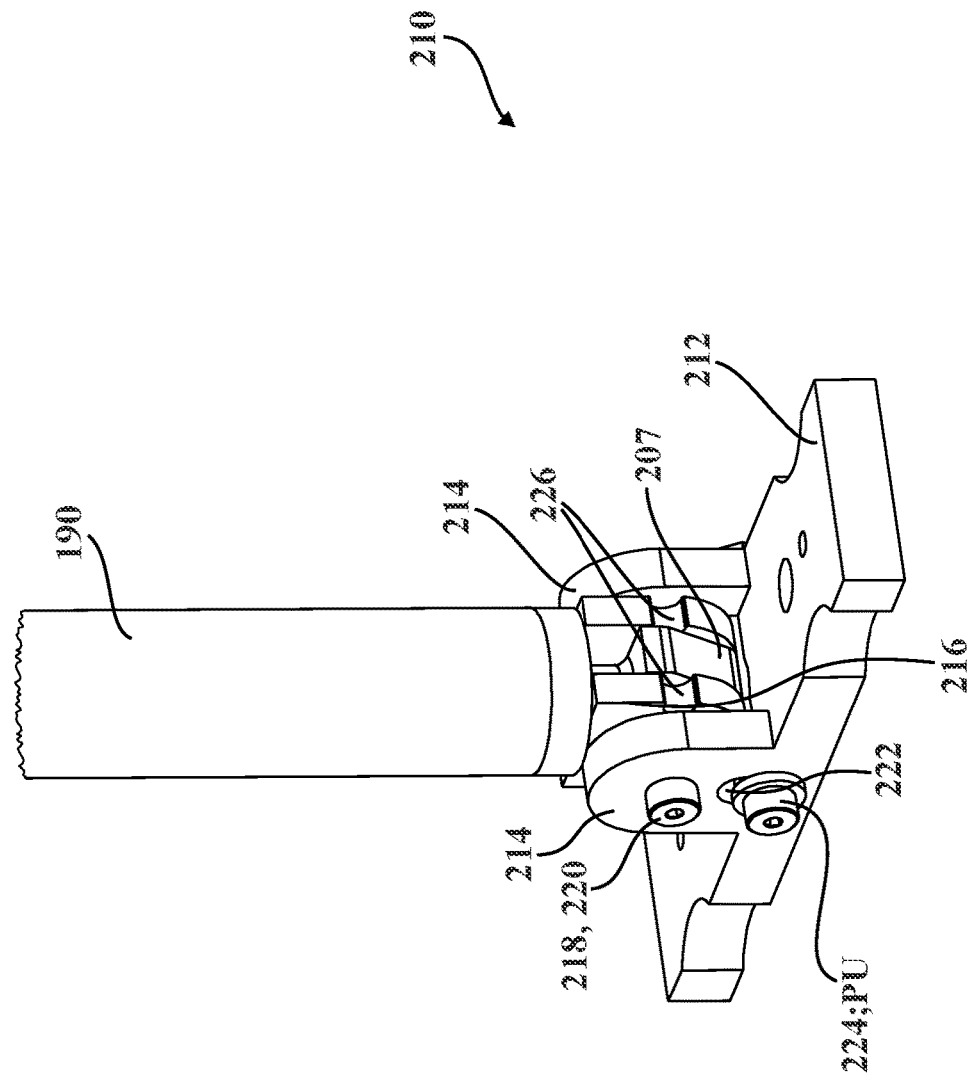
FIG. 9B is a perspective view of the pivot assembly with the safety pin in an activated state and the movable rod in an unlocked position to allow the pivot assembly to pivot the extension rod from a deployed position to a stowed position.
Figure 9C:
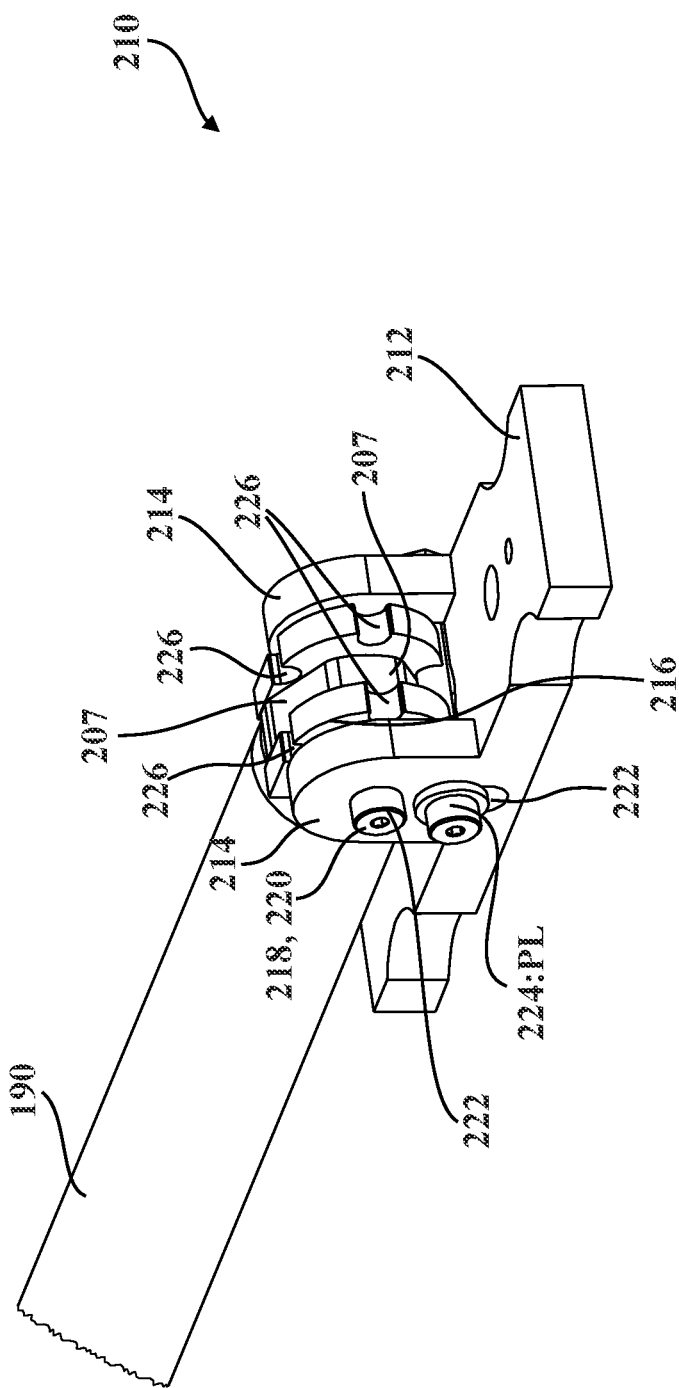
FIG. 9C is a perspective view of the pivot assembly with the extension rod in the stowed position and the movable rod in a locked position to prevent operation of the pivot assembly.
Figure 10:
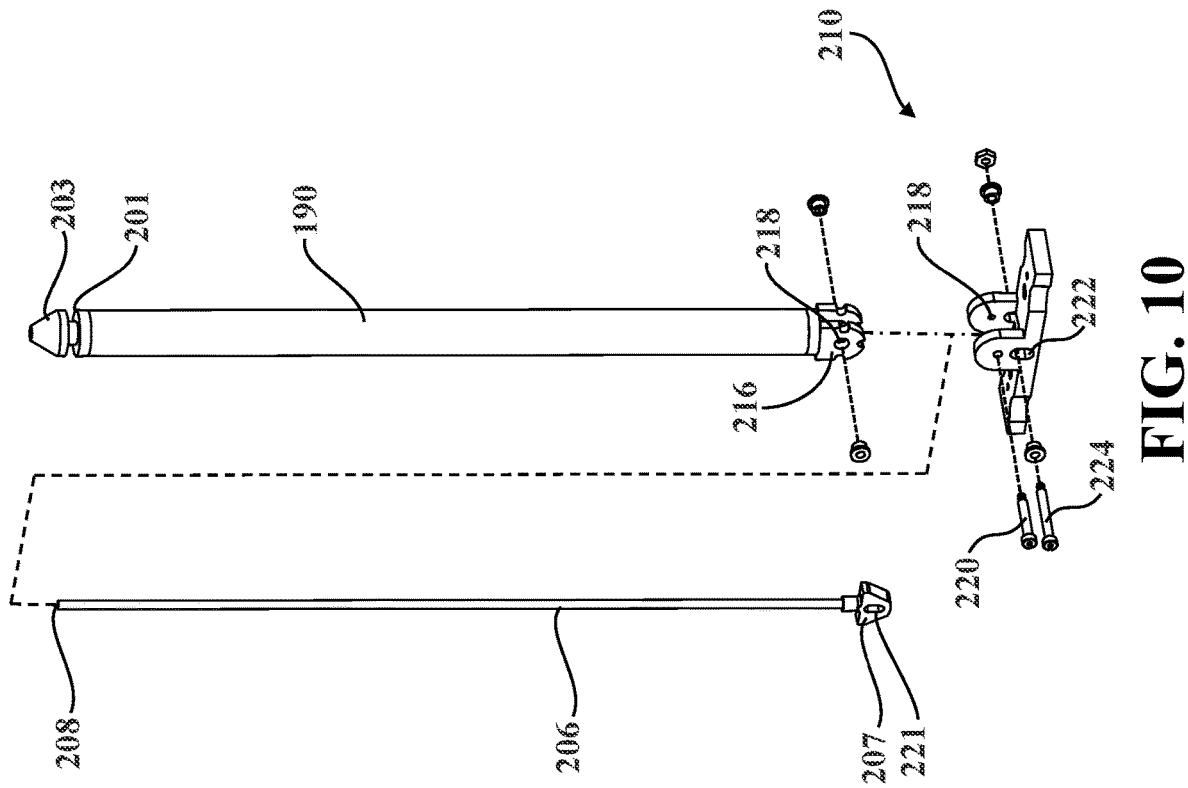
FIG. 10 is an exploded, perspective view of the pivot assembly with the safety pin shown outside the extension rod.

In some versions, with reference to FIGS. 9-10, the pivot assembly 204 includes a base assembly 210. The base assembly 210 includes a platform 212 that is coupled with the support plate 178. The platform 212 includes two braces 214 extending from the platform 212. The pivot assembly 204 further includes two indexers 216 coupled to the extension rod 190. The braces 214 and the indexers 216 each include a first bore 218 that aligns and allows a fixed rod 220 to extend the through the braces 214 and the indexers 216. The braces 214 each further include a slot 222, and the pusher 207 includes a pusher slot 221, that permits a movable rod 224 to pass through the slots 222 and the pusher slot 221. The indexers 216 also include a respective plurality of notches 226 that receive the movable rod 224. The movable rod 224 can be moved between a locked position PL and an unlocked position PL. In the locked position PL, the movable rod 224 is engaged with one of the plurality of notches 226 of each of the indexers 216 and the pivot assembly 204 is prevented from pivoting. Here, it will be appreciated that engagement of the movable rod 224 with the notches 226 of the indexers 216 maintains the pivot assembly 204 in either the deployed position PD (see FIG. 1C; see also FIG. 9A) or the stowed position (see FIG. 1D; see also FIG. 9C). When the movable rod 224 is in the unlocked position PU, the pivot assembly 204 is free to pivot when acted on by the user. The movable rod 224 is urged out of engagement with the notches 226 via the pusher 207, which is coupled to the safety pin 206 as noted above. Here, engagement with the safety pin 206 places the movable rod 224 into the unlocked position PL which, in turns, allows the pivot assembly 204 to be pivoted. In some versions, the movable rod 224 is biased (e.g., via a biasing element; not shown in detail) towards engagement with the notches 226 (not shown in detail).

Several instances have been discussed in the foregoing description. However, the aspects discussed herein are not intended to be exhaustive or limit the disclosure to any particular form. Various modifications to these aspects will be readily apparent to those skilled in the art, and the generic principles defined herein may be applied to other aspects without departing from the scope of the disclosure. The terminology that has been used is intended to be in the nature of words of description rather than of limitation. Many modifications and variations are possible in light of the above teachings and the disclosure may be practiced otherwise than as specifically described.

What is claimed is:

1. A patient support apparatus for concurrently transporting a patient and a medical device, the patient support apparatus comprising:
a base arranged for movement along floor surfaces;
an intermediate frame coupled to the base and defining a patient support deck for supporting a patient; and
a support assembly coupled to the intermediate frame for supporting the medical device for concurrent movement with the patient support apparatus, the support assembly including:
a track operatively attached to the intermediate frame and extending between a first track end and a second track end and with at least one curvilinear region defined therebetween,
a mount configured to support the medical device,
a carrier supporting the mount and coupled to the track for selective movement about the track between the first track end and the second track end, wherein the carrier comprises a first rail car having at least one first car roller disposed in sliding engagement with the track, and
a retainer operatively attached to the carrier and including a user interface, the retainer being operable between:
an engaged state to inhibit relative movement of the carrier along the track between the first track end and the second track end, and
a disengaged state to permit movement of the carrier along the track between the first track end and the second track end, the retainer moving from the engaged state to the disengaged state in response to user engagement with the user interface.

2. The patient support apparatus as set forth in claim 1 wherein the track further defines a first linear region adjacent to the first track end and a second linear region adjacent to the second track end.

3. The patient support apparatus as set forth in claim 2 wherein the track includes one curvilinear region that connects the first linear region and the second linear region.

4. The patient support apparatus as set forth in claim 3 wherein the first and second linear regions are substantially parallel to each other.

5. The patient support apparatus as set forth in claim 4 wherein the first and second linear regions are spaced laterally from each other.

6. The patient support apparatus as set forth in claim 2:
wherein the intermediate frame defines a first side and a second side opposite the first side;
wherein the patient support apparatus further comprises a first rail coupled to the first side and a second rail coupled to the second side; and
wherein the first linear region of the track is coupled to and substantially parallel with the first rail and the second linear region of the track is coupled to and substantially parallel with the second rail.

7. The patient support apparatus as set forth in claim 1 wherein the intermediate frame extends longitudinally between a head end and foot end, with the support assembly coupled to the intermediate frame adjacent the foot end.

8. The patient support apparatus as set forth in claim 1 wherein the carrier comprises a plurality of rollers engaged with the track for selective movement between the first track end and the second track end.

9. The patient support apparatus as set forth in claim 1 wherein the carrier further comprises a second rail car spaced from and coupled to the first rail car and having at least one second car roller disposed in sliding engagement with the track.

10. The patient support apparatus as set forth in claim 9 wherein the first rail car includes a pair of first car rollers each disposed in sliding engagement with the track and the second rail car includes a pair of second car rollers each disposed in sliding engagement with the track.

11. The patient support apparatus as set forth in claim 9 wherein the carrier comprises a support plate coupling the first and second rail cars.

12. The patient support apparatus as set forth in claim 11, wherein the first rail car is pivotably coupled to the support plate about a first car axis, and wherein the second rail car is pivotably coupled to the support plate about a second car axis spaced from the first car axis.

13. The patient support apparatus as set forth in claim 12 wherein the support plate defines a first seat arranged about the first car axis, and defines a second seat arranged about the second car axis, and wherein a first bearing is at least partially disposed in the first seat and a second bearing is at least partially disposed in the second seat for allowing the first and second rail cars to pivot independent of each other relative to the support plate.

14. The patient support apparatus as set forth in claim 13 wherein the first and second rail cars define respective top surfaces each facing the mount, with at least one limiter extending from the top surface of the first and second rail cars for limiting pivot motion of the support plate.

15. The patient support apparatus as set forth in claim 11 further comprising an extension rod coupling the mount to the support plate and extending between the carrier and the retainer.

16. The patient support apparatus as set forth in claim 15 wherein the user interface is operatively coupled to the extension rod.

17. The patient support apparatus as set forth in claim 15 further comprising a pivot assembly interposed between the extension rod and the support plate to permit selective movement between, wherein the extension rod extends generally horizontal relative to the intermediate frame when the extension rod is in a stowed position.

18. The patient support apparatus as set forth in claim 11 wherein the user interface includes a handle to permit the user to simultaneously engage the handle and move the retainer from the engaged state to the disengaged state and move the support assembly along the track between the ends.

19. The patient support apparatus as set forth in claim 1 wherein the track defines a plurality of apertures, and the patient support apparatus includes a pin supported by the carrier and movable between a first pin position and a second pin position, and wherein the pin is engaged in one of the plurality of apertures in the first pin position and released from the aperture in the second pin position.

20. The patient support apparatus as set forth in claim 17 further comprising an equipment frame for securing the medical device, with a receptacle coupled to the equipment frame for releasably engaging the equipment frame from the mount and exposing an activation mechanism for the pivot assembly upon removal of the mount.

21. A patient support apparatus for concurrently transporting a patient and a medical device, the patient support apparatus comprising:
- a base arranged for movement along floor surfaces;
- an intermediate frame coupled to the base and defining a patient support deck for supporting a patient; and
- a support assembly coupled to the intermediate frame for supporting the medical device for concurrent movement with the patient support apparatus, the support assembly including:
  - a track operatively attached to the intermediate frame and extending between a first track end on a first lateral side and a second track end on a second lateral side with at least one curvilinear region extending between the first lateral side and the second lateral side,
  - a mount configured to support the medical device,
  - a carrier supporting the mount and slidably coupled to the track for selective movement about the track continuously between the first track end and the second track end, and
  - a retainer operatively attached to the carrier and including a user interface, the retainer being operable between:
    - an engaged state to inhibit relative movement of the carrier along the track between the first track end and the second track end, and
    - a disengaged state to permit movement of the carrier along the track between the first track end and the second track end, the retainer moving from the engaged state to the disengaged state in response to user engagement with the user interface.

\* \* \* \* \*